US012605528B2

(12) United States Patent
Howell et al.

(10) Patent No.: US 12,605,528 B2
(45) Date of Patent: Apr. 21, 2026

(54) TWO-PIECE RAPIDLY INSERTABLE CENTRAL CATHETERS, INTRODUCERS THEREFOR, AND METHODS THEREOF

(71) Applicant: Bard Access Systems, Inc., Salt Lake City, UT (US)

(72) Inventors: Glade H. Howell, Draper, UT (US); Jason R. Stats, Layton, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 87 days.

(21) Appl. No.: 17/390,682

(22) Filed: Jul. 30, 2021

(65) Prior Publication Data

US 2022/0032013 A1 Feb. 3, 2022

Related U.S. Application Data

(60) Provisional application No. 63/059,798, filed on Jul. 31, 2020.

(51) Int. Cl.
*A61M 25/06* (2006.01)
*A61M 5/14* (2006.01)
(Continued)

(52) U.S. Cl.
CPC ........ *A61M 25/0668* (2013.01); *A61M 5/178* (2013.01); *A61M 25/0054* (2013.01);
(Continued)

(58) Field of Classification Search
CPC .............. A61M 5/178; A61M 25/0097; A61M 25/0606; A61M 2025/0681;
(Continued)

(56) References Cited

U.S. PATENT DOCUMENTS 1,013,691 A 1/1912 Shields
3,225,762 A 12/1965 Guttman
(Continued)

FOREIGN PATENT DOCUMENTS

DE 202012006191 U1 7/2012
EP 0653220 A1 5/1995
(Continued)

OTHER PUBLICATIONS

PCT/US2020/048583 filed Aug. 28, 2020 International Search Report and Written Opinion dated Nov. 13, 2020.
(Continued)

*Primary Examiner* — Michael J Tsai
*Assistant Examiner* — Kathleen Paige Farrell
(74) *Attorney, Agent, or Firm* — Rutan & Tucker LLP

(57) ABSTRACT

Disclosed are two-piece rapidly insertable central catheter ("RICCs"), introducers, and methods. For example, an introducer and a distal catheter piece of a RICC can be combined in an introducer assembly configured to be actuated with a single finger of a hand while the introducer is held between a thumb and another finger or fingers of the same hand. A catheter-advancement hub of the introducer includes a manifold coupled to a proximal portion of a distal catheter-hub piece of the distal catheter piece. An introducer needle of a syringe of the introducer has a needle shaft extending through the manifold and a distal end of the distal catheter piece. An introducer housing is over a syringe tip, the manifold, and the proximal portion of the distal catheter piece. The introducer housing of the introducer configured to provide column strength to a catheter tube of the distal catheter piece during a venipuncture.

34 Claims, 18 Drawing Sheets

(51) Int. Cl.

| | |
|---|---|
| *A61M 5/178* | (2006.01) |
| *A61M 25/00* | (2006.01) |
| *A61M 25/09* | (2006.01) |

(52) U.S. Cl.

CPC .... *A61M 25/0097* (2013.01); *A61M 25/0606* (2013.01); *A61M 25/09* (2013.01); *A61M 2005/1402* (2013.01); *A61M 2025/0006* (2013.01); *A61M 25/0032* (2013.01); *A61M 2025/0681* (2013.01)

(58) Field of Classification Search

CPC ...... A61M 25/0054; A61M 2025/0006; A61M 25/09041; A61M 25/0693; A61M 2025/0183; A61M 25/09; A61M 25/0631; A61M 25/0618; A61M 2025/09125; A61M 25/0026; A61M 2025/09116; A61M 2039/062; A61M 25/0169; A61M 25/01; A61M 25/0668

See application file for complete search history.

(56) References Cited

U.S. PATENT DOCUMENTS

| | | | |
|---|---|---|---|
| 3,325,061 | A | 6/1967 | Ellsworth |
| 3,382,872 | A | 5/1968 | Rubin |
| 3,570,485 | A | 3/1971 | Reilly |
| 3,890,976 | A | 6/1975 | Bazell et al. |
| 3,991,762 | A | 11/1976 | Radford |
| 4,205,675 | A | 6/1980 | Vaillancourt |
| 4,292,970 | A | 10/1981 | Hession, Jr. |
| 4,468,224 | A | 8/1984 | Enzmann et al. |
| 4,484,915 | A | 11/1984 | Tartaglia |
| 4,525,157 | A | 6/1985 | Vaillancourt |
| 4,581,019 | A | 4/1986 | Curelaru et al. |
| 4,582,181 | A | 4/1986 | Samson |
| 4,594,073 | A | 6/1986 | Stine |
| 4,702,735 | A | 10/1987 | Luther et al. |
| 4,743,265 | A | 5/1988 | Whitehouse et al. |
| 4,766,908 | A | 8/1988 | Clement |
| 4,863,432 | A | 9/1989 | Kvalo |
| 4,935,008 | A | 6/1990 | Lewis, Jr. |
| 4,950,252 | A | 8/1990 | Luther et al. |
| 4,957,489 | A | 9/1990 | Cameron et al. |
| 4,994,040 | A | 2/1991 | Cameron et al. |
| 5,017,259 | A | 5/1991 | Kohsai |
| 5,040,548 | A | 8/1991 | Yock |
| 5,057,073 | A | 10/1991 | Martin |
| 5,112,312 | A | 5/1992 | Luther |
| 5,115,816 | A | 5/1992 | Lee |
| 5,120,317 | A | 6/1992 | Luther |
| 5,158,544 | A | 10/1992 | Weinstein |
| 5,167,634 | A | 12/1992 | Corrigan, Jr. et al. |
| 5,188,593 | A | 2/1993 | Martin |
| 5,195,962 | A | 3/1993 | Martin et al. |
| 5,207,650 | A | 5/1993 | Martin |
| RE34,416 | E | 10/1993 | Lemieux |
| 5,267,958 | A | 12/1993 | Buchbinder et al. |
| 5,290,241 | A | 3/1994 | Kraus et al. |
| 5,295,970 | A | 3/1994 | Clinton et al. |
| 5,306,247 | A | 4/1994 | Pfenninger |
| 5,312,361 | A | 5/1994 | Zadini et al. |
| 5,322,512 | A | 6/1994 | Mohiuddin |
| 5,328,472 | A | 7/1994 | Steinke et al. |
| 5,350,358 | A | 9/1994 | Martin |
| 5,358,495 | A | 10/1994 | Lynn |
| 5,364,355 | A | 11/1994 | Alden et al. |
| 5,368,567 | A | 11/1994 | Lee |
| 5,378,230 | A | 1/1995 | Mahurkar |
| 5,380,290 | A | 1/1995 | Makower et al. |
| 5,389,087 | A | 2/1995 | Miraki |
| 5,439,449 | A | 8/1995 | Mapes et al. |
| 5,443,457 | A | 8/1995 | Ginn et al. |
| 5,460,185 | A | 10/1995 | Johnson et al. |
| 5,489,271 | A | 2/1996 | Andersen |
| 5,573,520 | A | 11/1996 | Schwartz et al. |
| 5,584,813 | A | 12/1996 | Livingston et al. |
| 5,683,370 | A | 11/1997 | Luther et al. |
| 5,713,876 | A | 2/1998 | Bogert et al. |
| 5,718,678 | A | 2/1998 | Fleming, III |
| 5,772,636 | A | 6/1998 | Brimhall et al. |
| 5,885,251 | A | 3/1999 | Luther |
| 5,919,164 | A | 7/1999 | Andersen |
| 5,921,971 | A | 7/1999 | Agro et al. |
| 5,947,940 | A | 9/1999 | Beisel |
| 5,951,518 | A | 9/1999 | Licata et al. |
| 5,957,893 | A | 9/1999 | Luther et al. |
| 5,971,957 | A | 10/1999 | Luther et al. |
| 6,159,198 | A | 12/2000 | Gardeski et al. |
| 6,197,007 | B1 | 3/2001 | Thorne et al. |
| 6,206,849 | B1 | 3/2001 | Martin et al. |
| 6,228,062 | B1 | 5/2001 | Howell et al. |
| 6,273,874 | B1 | 8/2001 | Parris |
| 6,475,187 | B1 | 11/2002 | Gerberding |
| 6,533,782 | B2 | 3/2003 | Howell et al. |
| 6,551,284 | B1 | 4/2003 | Greenberg et al. |
| 6,606,515 | B1 | 8/2003 | Windheuser et al. |
| 6,616,630 | B1 | 9/2003 | Woehr et al. |
| 6,626,869 | B1 | 9/2003 | Bint |
| 6,638,252 | B2 | 10/2003 | Moulton et al. |
| 6,716,228 | B2 | 4/2004 | Tal |
| 6,726,659 | B1 | 4/2004 | Stocking et al. |
| 6,819,951 | B2 | 11/2004 | Patel et al. |
| 6,821,287 | B1 | 11/2004 | Jang |
| 6,926,692 | B2 | 8/2005 | Katoh et al. |
| 6,962,575 | B2 | 11/2005 | Tal |
| 6,991,625 | B1 | 1/2006 | Gately et al. |
| 6,994,693 | B2 | 2/2006 | Tal |
| 6,999,809 | B2 | 2/2006 | Currier et al. |
| 7,025,746 | B2 | 4/2006 | Tal |
| 7,029,467 | B2 | 4/2006 | Currier et al. |
| 7,037,293 | B2 | 5/2006 | Carrillo et al. |
| 7,074,231 | B2 | 7/2006 | Jang |
| 7,094,222 | B1 | 8/2006 | Siekas et al. |
| 7,141,050 | B2 | 11/2006 | Deal et al. |
| 7,144,386 | B2 | 12/2006 | Korkor et al. |
| 7,311,697 | B2 | 12/2007 | Osborne |
| 7,364,566 | B2 | 4/2008 | Elkins et al. |
| 7,377,910 | B2 | 5/2008 | Katoh et al. |
| 7,390,323 | B2 | 6/2008 | Jang |
| D600,793 | S | 9/2009 | Bierman et al. |
| D601,242 | S | 9/2009 | Bierman et al. |
| D601,243 | S | 9/2009 | Bierman et al. |
| 7,594,911 | B2 | 9/2009 | Powers et al. |
| 7,691,093 | B2 | 4/2010 | Brimhall |
| 7,722,567 | B2 | 5/2010 | Tal |
| D617,893 | S | 6/2010 | Bierman et al. |
| D624,643 | S | 9/2010 | Bierman et al. |
| 7,819,889 | B2 | 10/2010 | Healy et al. |
| 7,857,788 | B2 | 12/2010 | Racz |
| D630,729 | S | 1/2011 | Bierman et al. |
| 7,909,797 | B2 | 3/2011 | Kennedy, II et al. |
| 7,909,811 | B2 | 3/2011 | Agro et al. |
| 7,922,696 | B2 | 4/2011 | Tal et al. |
| 7,938,820 | B2 | 5/2011 | Webster et al. |
| 7,967,834 | B2 | 6/2011 | Tal et al. |
| 7,976,511 | B2 | 7/2011 | Fojtik |
| 7,985,204 | B2 | 7/2011 | Katoh et al. |
| 8,073,517 | B1 | 12/2011 | Burchman |
| 8,105,286 | B2 | 1/2012 | Anderson et al. |
| 8,192,402 | B2 | 6/2012 | Anderson et al. |
| 8,202,251 | B2 | 6/2012 | Bierman et al. |
| 8,206,356 | B2 | 6/2012 | Katoh et al. |
| 8,361,011 | B2 | 1/2013 | Mendels |
| 8,372,107 | B2 | 2/2013 | Tupper |
| 8,377,006 | B2 | 2/2013 | Tal et al. |
| 8,454,577 | B2 | 6/2013 | Joergensen et al. |
| 8,585,858 | B2 | 11/2013 | Kronfeld et al. |
| 8,657,790 | B2 | 2/2014 | Tal et al. |
| 8,672,888 | B2 | 3/2014 | Tal |
| 8,696,645 | B2 | 4/2014 | Tal et al. |
| 8,784,362 | B2 | 7/2014 | Boutilette et al. |
| 8,827,958 | B2 | 9/2014 | Bierman et al. |
| 8,876,704 | B2 | 11/2014 | Golden et al. |

(56) References Cited

U.S. PATENT DOCUMENTS

| | | |
|---|---|---|
| 8,882,713 B1 | 11/2014 | Call et al. |
| 8,900,192 B2 | 12/2014 | Anderson et al. |
| 8,900,207 B2 | 12/2014 | Uretsky |
| 8,915,884 B2 | 12/2014 | Tal et al. |
| 8,956,327 B2 | 2/2015 | Bierman et al. |
| 9,023,093 B2 | 5/2015 | Pal |
| 9,067,023 B2* | 6/2015 | Bertocci ............. A61M 5/3148 |
| 9,126,012 B2* | 9/2015 | McKinnon ........ A61M 25/0097 |
| 9,138,252 B2 | 9/2015 | Bierman et al. |
| 9,180,275 B2 | 11/2015 | Helm |
| 9,265,920 B2 | 2/2016 | Rundquist et al. |
| 9,272,121 B2 | 3/2016 | Piccagli |
| 9,445,734 B2 | 9/2016 | Grunwald |
| 9,522,254 B2 | 12/2016 | Belson |
| 9,554,785 B2 | 1/2017 | Walters et al. |
| 9,566,087 B2 | 2/2017 | Bierman et al. |
| 9,675,784 B2 | 6/2017 | Belson |
| 9,713,695 B2 | 7/2017 | Bunch et al. |
| 9,764,117 B2 | 9/2017 | Bierman et al. |
| 9,770,573 B2 | 9/2017 | Golden et al. |
| 9,814,861 B2 | 11/2017 | Boutillette et al. |
| 9,820,845 B2 | 11/2017 | von Lehe et al. |
| 9,861,383 B2 | 1/2018 | Clark |
| 9,872,971 B2 | 1/2018 | Blanchard |
| 9,884,169 B2 | 2/2018 | Bierman et al. |
| 9,889,275 B2 | 2/2018 | Voss et al. |
| 9,913,585 B2 | 3/2018 | McCaffrey et al. |
| 9,913,962 B2 | 3/2018 | Tal et al. |
| 9,981,113 B2 | 5/2018 | Bierman |
| 10,010,312 B2 | 7/2018 | Tegels |
| 10,065,020 B2 | 9/2018 | Gaur |
| 10,086,170 B2 | 10/2018 | Chhikara et al. |
| 10,098,724 B2 | 10/2018 | Adams et al. |
| 10,111,683 B2 | 10/2018 | Tsamir et al. |
| 10,118,020 B2 | 11/2018 | Avneri et al. |
| 10,130,269 B2 | 11/2018 | McCaffrey et al. |
| 10,220,184 B2 | 3/2019 | Clark |
| 10,220,191 B2 | 3/2019 | Belson et al. |
| 10,265,508 B2 | 4/2019 | Baid |
| 10,271,873 B2 | 4/2019 | Steingisser et al. |
| 10,376,675 B2 | 8/2019 | Mitchell et al. |
| 10,675,440 B2 | 6/2020 | Abitabilo et al. |
| 10,688,281 B2 | 6/2020 | Blanchard et al. |
| 10,806,901 B2 | 10/2020 | Burkholz et al. |
| 10,926,060 B2 | 2/2021 | Stern et al. |
| 11,260,206 B2 | 3/2022 | Stone et al. |
| 11,400,260 B2 | 8/2022 | Huang et al. |
| 11,759,607 B1 | 9/2023 | Biancarelli |
| 2002/0040231 A1 | 4/2002 | Wysoki |
| 2002/0045843 A1 | 4/2002 | Barker et al. |
| 2002/0123755 A1 | 9/2002 | Lowe et al. |
| 2002/0198492 A1 | 12/2002 | Miller et al. |
| 2003/0036712 A1 | 2/2003 | Heh et al. |
| 2003/0060863 A1 | 3/2003 | Dobak |
| 2003/0088212 A1 | 5/2003 | Tal |
| 2003/0100849 A1 | 5/2003 | Jang |
| 2003/0153874 A1 | 8/2003 | Tal |
| 2003/0158514 A1 | 8/2003 | Tal |
| 2004/0015138 A1 | 1/2004 | Currier et al. |
| 2004/0049157 A1 | 3/2004 | Plishka et al. |
| 2004/0064086 A1 | 4/2004 | Gottlieb et al. |
| 2004/0092879 A1 | 5/2004 | Kraus et al. |
| 2004/0116864 A1 | 6/2004 | Boudreaux |
| 2004/0116901 A1 | 6/2004 | Appling |
| 2004/0167478 A1 | 8/2004 | Mooney et al. |
| 2004/0193093 A1 | 9/2004 | Desmond |
| 2004/0230178 A1 | 11/2004 | Wu |
| 2005/0004554 A1 | 1/2005 | Osborne |
| 2005/0120523 A1 | 6/2005 | Schweikert |
| 2005/0131343 A1* | 6/2005 | Abrams et al. ... A61M 25/0147 |
| | | 604/95.04 |
| 2005/0148936 A1 | 7/2005 | Moss |
| 2005/0215956 A1 | 9/2005 | Nerney |
| 2005/0215958 A1 | 9/2005 | Hawthorne |
| 2005/0245882 A1 | 11/2005 | Elkins et al. |
| 2005/0283221 A1 | 12/2005 | Mann et al. |
| 2006/0009740 A1 | 1/2006 | Higgins et al. |
| 2006/0116629 A1 | 6/2006 | Tal et al. |
| 2006/0129100 A1 | 6/2006 | Tal |
| 2006/0129130 A1 | 6/2006 | Tal et al. |
| 2006/0135973 A1 | 6/2006 | Hawkins et al. |
| 2007/0276288 A1 | 11/2007 | Khaw |
| 2008/0045894 A1 | 2/2008 | Perchik et al. |
| 2008/0091137 A1 | 4/2008 | Reavill |
| 2008/0125744 A1 | 5/2008 | Treacy |
| 2008/0125748 A1 | 5/2008 | Patel |
| 2008/0132850 A1 | 6/2008 | Fumiyama et al. |
| 2008/0262430 A1 | 10/2008 | Anderson et al. |
| 2008/0262431 A1 | 10/2008 | Anderson et al. |
| 2008/0294111 A1 | 11/2008 | Tal et al. |
| 2008/0312578 A1 | 12/2008 | DeFonzo et al. |
| 2008/0319387 A1 | 12/2008 | Amisar et al. |
| 2009/0131872 A1 | 5/2009 | Popov |
| 2009/0187147 A1 | 7/2009 | Kurth et al. |
| 2009/0221961 A1 | 9/2009 | Tal et al. |
| 2009/0270889 A1 | 10/2009 | Tal et al. |
| 2009/0292272 A1 | 11/2009 | McKinnon |
| 2010/0030154 A1 | 2/2010 | Duffy |
| 2010/0256487 A1 | 10/2010 | Hawkins et al. |
| 2010/0298839 A1 | 11/2010 | Castro |
| 2010/0305474 A1 | 12/2010 | DeMars et al. |
| 2011/0004162 A1 | 1/2011 | Tal |
| 2011/0009827 A1 | 1/2011 | Bierman et al. |
| 2011/0021994 A1 | 1/2011 | Anderson et al. |
| 2011/0066142 A1 | 3/2011 | Tal et al. |
| 2011/0071502 A1 | 3/2011 | Asai |
| 2011/0144620 A1 | 6/2011 | Tal |
| 2011/0152836 A1 | 6/2011 | Riopelle et al. |
| 2011/0190778 A1 | 8/2011 | Arpasi et al. |
| 2011/0202006 A1 | 8/2011 | Bierman et al. |
| 2011/0230844 A1 | 9/2011 | Shaw et al. |
| 2011/0251559 A1 | 10/2011 | Tal et al. |
| 2011/0270192 A1 | 11/2011 | Anderson et al. |
| 2012/0016346 A1 | 1/2012 | Steinmetz et al. |
| 2012/0041371 A1 | 2/2012 | Tal et al. |
| 2012/0065590 A1 | 3/2012 | Bierman et al. |
| 2012/0078231 A1 | 3/2012 | Hoshinouchi |
| 2012/0130411 A1 | 5/2012 | Tal et al. |
| 2012/0130415 A1 | 5/2012 | Tal et al. |
| 2012/0157854 A1 | 6/2012 | Kurrus et al. |
| 2012/0215171 A1 | 8/2012 | Christiansen |
| 2012/0220942 A1 | 8/2012 | Hall et al. |
| 2012/0226239 A1 | 9/2012 | Green |
| 2012/0283640 A1 | 11/2012 | Anderson et al. |
| 2012/0316500 A1 | 12/2012 | Bierman et al. |
| 2013/0046241 A1 | 2/2013 | Okamura et al. |
| 2013/0053763 A1 | 2/2013 | Makino et al. |
| 2013/0053826 A1 | 2/2013 | Shevgoor |
| 2013/0123704 A1 | 5/2013 | Bierman et al. |
| 2013/0158338 A1 | 6/2013 | Kelly et al. |
| 2013/0158506 A1 | 6/2013 | Harris et al. |
| 2013/0188291 A1 | 7/2013 | Vardiman |
| 2013/0237931 A1 | 9/2013 | Tal et al. |
| 2013/0306079 A1 | 11/2013 | Tracy |
| 2014/0025036 A1 | 1/2014 | Bierman et al. |
| 2014/0081210 A1 | 3/2014 | Bierman et al. |
| 2014/0094774 A1* | 4/2014 | Blanchard ......... A61M 25/0105 |
| 2014/0100552 A1 | 4/2014 | Gallacher et al. |
| 2014/0110296 A1 | 4/2014 | Terzibashian |
| 2014/0171833 A1 | 6/2014 | Matsuno et al. |
| 2014/0188211 A1 | 7/2014 | Roeder et al. |
| 2014/0207052 A1 | 7/2014 | Tal et al. |
| 2014/0207069 A1 | 7/2014 | Bierman et al. |
| 2014/0214005 A1 | 7/2014 | Belson |
| 2014/0221831 A1 | 8/2014 | Kurrus et al. |
| 2014/0257111 A1 | 9/2014 | Yamashita et al. |
| 2014/0276432 A1 | 9/2014 | Bierman et al. |
| 2014/0276599 A1 | 9/2014 | Cully et al. |
| 2015/0011834 A1 | 1/2015 | Ayala et al. |
| 2015/0080939 A1 | 3/2015 | Adams et al. |
| 2015/0094653 A1 | 4/2015 | Pacheco et al. |
| 2015/0112307 A1 | 4/2015 | Margolis |
| 2015/0112310 A1 | 4/2015 | Call et al. |
| 2015/0119806 A1 | 4/2015 | Blanchard et al. |

(56) References Cited

U.S. PATENT DOCUMENTS

| | | |
|---|---|---|
| 2015/0126930 A1 | 5/2015 | Bierman et al. |
| 2015/0148595 A1 | 5/2015 | Bagwell et al. |
| 2015/0157829 A1 | 6/2015 | Bunch et al. |
| 2015/0190168 A1 | 7/2015 | Bierman et al. |
| 2015/0196210 A1 | 7/2015 | McCaffrey et al. |
| 2015/0224287 A1 | 8/2015 | Bian et al. |
| 2015/0231364 A1 | 8/2015 | Blanchard et al. |
| 2015/0283357 A1 | 10/2015 | Lampropoulos et al. |
| 2015/0290431 A1 | 10/2015 | Hall et al. |
| 2015/0297868 A1 | 10/2015 | Tal et al. |
| 2015/0306356 A1 | 10/2015 | Gill |
| 2015/0320969 A1 | 11/2015 | Haslinger et al. |
| 2015/0320977 A1 | 11/2015 | Vitullo et al. |
| 2015/0351793 A1 | 12/2015 | Bierman et al. |
| 2015/0359549 A1 | 12/2015 | Lenker et al. |
| 2015/0359998 A1 | 12/2015 | Carmel et al. |
| 2016/0001046 A1 | 1/2016 | Tietze |
| 2016/0030716 A1 | 2/2016 | Mallin et al. |
| 2016/0082223 A1 | 3/2016 | Barnell |
| 2016/0114124 A1 | 4/2016 | Tal |
| 2016/0158523 A1 | 6/2016 | Helm |
| 2016/0220786 A1 | 8/2016 | Mitchell et al. |
| 2016/0220811 A1 | 8/2016 | Spotnitz et al. |
| 2016/0242661 A1 | 8/2016 | Fischell et al. |
| 2016/0256101 A1 | 9/2016 | Aharoni et al. |
| 2016/0325073 A1 | 11/2016 | Davies et al. |
| 2016/0331938 A1 | 11/2016 | Blanchard et al. |
| 2016/0338728 A1 | 11/2016 | Tal |
| 2016/0346503 A1 | 12/2016 | Jackson et al. |
| 2017/0028135 A1 | 2/2017 | Fransson et al. |
| 2017/0035990 A1 | 2/2017 | Swift |
| 2017/0072165 A1 | 3/2017 | Lim et al. |
| 2017/0120000 A1* | 5/2017 | Osypka et al. ....... A61M 39/20 |
| 2017/0120014 A1 | 5/2017 | Harding et al. |
| 2017/0120034 A1 | 5/2017 | Kaczorowski |
| 2017/0128700 A1 | 5/2017 | Roche Rebollo |
| 2017/0156987 A1 | 6/2017 | Babbs et al. |
| 2017/0172653 A1 | 6/2017 | Urbanski et al. |
| 2017/0182293 A1 | 6/2017 | Chhikara et al. |
| 2017/0239443 A1 | 8/2017 | Abitabilo et al. |
| 2017/0259043 A1 | 9/2017 | Chan et al. |
| 2017/0273713 A1 | 9/2017 | Shah et al. |
| 2017/0274182 A1 | 9/2017 | O'Bryan et al. |
| 2017/0296792 A1 | 10/2017 | Ornelas Vargas et al. |
| 2017/0326339 A1 | 11/2017 | Bailey et al. |
| 2017/0361070 A1 | 12/2017 | Hivert |
| 2017/0368255 A1 | 12/2017 | Provost et al. |
| 2018/0001062 A1 | 1/2018 | O'Carrol et al. |
| 2018/0008294 A1 | 1/2018 | Garrison et al. |
| 2018/0021545 A1 | 1/2018 | Mitchell et al. |
| 2018/0116690 A1 | 5/2018 | Sarabia et al. |
| 2018/0117284 A1 | 5/2018 | Appling et al. |
| 2018/0133438 A1 | 5/2018 | Hulvershorn et al. |
| 2018/0154062 A1 | 6/2018 | DeFonzo et al. |
| 2018/0154112 A1* | 6/2018 | Chan et al. ....... A61M 25/0606 |
| 2018/0214674 A1 | 8/2018 | Ebnet et al. |
| 2018/0229004 A1 | 8/2018 | Blanchard et al. |
| 2018/0296799 A1* | 10/2018 | Horst et al. ....... A61M 25/0606 |
| 2018/0296804 A1 | 10/2018 | Bierman |
| 2018/0310955 A1 | 11/2018 | Lindekugel et al. |
| 2018/0369540 A1 | 12/2018 | Asai |
| 2019/0015646 A1 | 1/2019 | Matlock et al. |
| 2019/0021640 A1 | 1/2019 | Burkholz et al. |
| 2019/0038113 A1 | 2/2019 | Chu |
| 2019/0060616 A1 | 2/2019 | Solomon |
| 2019/0076167 A1 | 3/2019 | Fantuzzi et al. |
| 2019/0076628 A1 | 3/2019 | Anstett |
| 2019/0134349 A1 | 5/2019 | Cohn et al. |
| 2019/0192824 A1 | 6/2019 | Cordeiro et al. |
| 2019/0201665 A1 | 7/2019 | Turpin |
| 2019/0209812 A1 | 7/2019 | Burkholz et al. |
| 2019/0255294 A1 | 8/2019 | Mitchell et al. |
| 2019/0255298 A1 | 8/2019 | Mitchell et al. |
| 2019/0275303 A1 | 9/2019 | Tran et al. |
| 2019/0276268 A1 | 9/2019 | Akingba |
| 2019/0321590 A1 | 10/2019 | Burkholz et al. |
| 2019/0351196 A1 | 11/2019 | Ribelin et al. |
| 2020/0001051 A1* | 1/2020 | Huang et al. ..... A61M 25/0618 |
| 2020/0016374 A1 | 1/2020 | Burkholz et al. |
| 2020/0046948 A1 | 2/2020 | Burkholz et al. |
| 2020/0100716 A1 | 4/2020 | Devgon et al. |
| 2020/0129732 A1 | 4/2020 | Vogt et al. |
| 2020/0147349 A1* | 5/2020 | Holt ................. A61M 25/0606 |
| 2020/0197579 A1 | 6/2020 | Chu et al. |
| 2020/0197682 A1 | 6/2020 | Franklin et al. |
| 2020/0197684 A1 | 6/2020 | Wax |
| 2020/0237278 A1 | 7/2020 | Asbaghi |
| 2020/0359995 A1 | 11/2020 | Walsh et al. |
| 2021/0030944 A1 | 2/2021 | Cushen et al. |
| 2021/0060306 A1 | 3/2021 | Kumar |
| 2021/0069471 A1 | 3/2021 | Howell |
| 2021/0085927 A1 | 3/2021 | Howell |
| 2021/0100985 A1 | 4/2021 | Akcay et al. |
| 2021/0113809 A1 | 4/2021 | Howell |
| 2021/0113810 A1 | 4/2021 | Howell |
| 2021/0113816 A1 | 4/2021 | DiCianni |
| 2021/0121661 A1 | 4/2021 | Howell |
| 2021/0121667 A1 | 4/2021 | Howell |
| 2021/0228842 A1 | 7/2021 | Scherich et al. |
| 2021/0228843 A1 | 7/2021 | Howell et al. |
| 2021/0244920 A1 | 8/2021 | Kujawa et al. |
| 2021/0290898 A1 | 9/2021 | Burkholz |
| 2021/0290901 A1 | 9/2021 | Burkholz et al. |
| 2021/0290913 A1 | 9/2021 | Horst et al. |
| 2021/0322729 A1 | 10/2021 | Howell |
| 2021/0330941 A1* | 10/2021 | Howell et al. ........ A61M 25/06 |
| 2021/0330942 A1 | 10/2021 | Howell |
| 2021/0361915 A1 | 11/2021 | Howell et al. |
| 2021/0402149 A1 | 12/2021 | Howell |
| 2021/0402153 A1 | 12/2021 | Howell et al. |
| 2022/0001109 A1 | 1/2022 | Simon |
| 2022/0001138 A1 | 1/2022 | Howell |
| 2022/0032014 A1 | 2/2022 | Howell et al. |
| 2022/0062528 A1 | 3/2022 | Thornley et al. |
| 2022/0062596 A1 | 3/2022 | Ribelin et al. |
| 2022/0126064 A1 | 4/2022 | Tobin et al. |
| 2022/0193376 A1 | 6/2022 | Spataro et al. |
| 2022/0193377 A1 | 6/2022 | Haymond et al. |
| 2022/0193378 A1 | 6/2022 | Spataro et al. |
| 2022/0203075 A1 | 6/2022 | Murphy |
| 2022/0323723 A1 | 10/2022 | Spataro et al. |
| 2022/0331562 A1 | 10/2022 | Jaros et al. |
| 2022/0331563 A1 | 10/2022 | Papadia |
| 2023/0042898 A1 | 2/2023 | Howell et al. |
| 2023/0096377 A1 | 3/2023 | West et al. |
| 2023/0096740 A1 | 3/2023 | Bechstein et al. |
| 2023/0099654 A1 | 3/2023 | Blanchard et al. |
| 2023/0100482 A1 | 3/2023 | Howell |
| 2023/0101455 A1 | 3/2023 | Howell et al. |
| 2023/0102231 A1 | 3/2023 | Bechstein et al. |
| 2023/0173231 A1 | 6/2023 | Parikh et al. |
| 2023/0233814 A1 | 7/2023 | Howell et al. |
| 2023/0381459 A1 | 11/2023 | Belson et al. |
| 2023/0381481 A1 | 11/2023 | Pizzato |
| 2024/0009427 A1 | 1/2024 | Howell et al. |
| 2024/0050706 A1 | 2/2024 | Howell et al. |
| 2024/0198058 A1 | 6/2024 | Howell et al. |
| 2025/0001136 A1 | 1/2025 | Mitchell et al. |
| 2025/0065083 A1 | 2/2025 | Haymond et al. |
| 2025/0082906 A1 | 3/2025 | Howell et al. |
| 2025/0222237 A1 | 7/2025 | Spataro et al. |
| 2025/0235669 A1 | 7/2025 | Howell |

FOREIGN PATENT DOCUMENTS

| | | |
|---|---|---|
| EP | 0730880 A1 | 9/1996 |
| EP | 2061385 A1 | 5/2009 |
| EP | 1458437 B1 | 3/2010 |
| EP | 2248549 A2 | 11/2010 |
| EP | 2319576 A1 | 5/2011 |
| EP | 2366422 A1 | 9/2011 |
| EP | 2486880 A2 | 8/2012 |
| EP | 2486881 A2 | 8/2012 |
| EP | 2486951 A2 | 8/2012 |

(56) References Cited

FOREIGN PATENT DOCUMENTS

| | | | |
|---|---|---|---|
| EP | 2512576 | A2 | 10/2012 |
| EP | 2152348 | B1 | 2/2015 |
| EP | 3473291 | A1 | 4/2019 |
| EP | 3093038 | B1 | 5/2019 |
| EP | 2260897 | B1 | 9/2019 |
| EP | 3693051 | A1 | 8/2020 |
| GB | 1273547 | A | 5/1972 |
| JP | 2004248987 | A | 9/2004 |
| JP | 2008054859 | A | 3/2008 |
| WO | 94/21315 | A1 | 9/1994 |
| WO | 95/32009 | A2 | 11/1995 |
| WO | 98/44979 | A1 | 10/1998 |
| WO | 98/53871 | A1 | 12/1998 |
| WO | 9857685 | A1 | 12/1998 |
| WO | 99/12600 | A1 | 3/1999 |
| WO | 99/26681 | A1 | 6/1999 |
| WO | 00/06221 | A1 | 2/2000 |
| WO | 0054830 | A1 | 9/2000 |
| WO | 2003008020 | A1 | 1/2003 |
| WO | 2003057272 | A2 | 7/2003 |
| WO | 03/068073 | A1 | 8/2003 |
| WO | 2003066125 | A2 | 8/2003 |
| WO | 2005096778 | A2 | 10/2005 |
| WO | 2006055288 | A2 | 5/2006 |
| WO | 2006055780 | A2 | 5/2006 |
| WO | 2007046850 | A2 | 4/2007 |
| WO | 2008033983 | A1 | 3/2008 |
| WO | 2008092029 | A2 | 7/2008 |
| WO | 2008/131300 | A2 | 10/2008 |
| WO | 2008131289 | A2 | 10/2008 |
| WO | 2009114833 | A1 | 9/2009 |
| WO | 2009114837 | A2 | 9/2009 |
| WO | 2010/048449 | A2 | 4/2010 |
| WO | 2010056906 | A2 | 5/2010 |
| WO | 2010083467 | A2 | 7/2010 |
| WO | 2010/132608 | A2 | 11/2010 |
| WO | 2011081859 | A2 | 7/2011 |
| WO | 2011097639 | A2 | 8/2011 |
| WO | 2011109792 | A1 | 9/2011 |
| WO | 2011146764 | A1 | 11/2011 |
| WO | 2012068162 | A2 | 5/2012 |
| WO | 2012068166 | A2 | 5/2012 |
| WO | 2012135761 | A1 | 10/2012 |
| WO | 2012/154277 | A1 | 11/2012 |
| WO | 2012162677 | A1 | 11/2012 |
| WO | 2013026045 | A1 | 2/2013 |
| WO | 2013138519 | A1 | 9/2013 |
| WO | 2014006403 | A1 | 1/2014 |
| WO | 2014/100392 | A1 | 6/2014 |
| WO | 2014113257 | A2 | 7/2014 |
| WO | 2014152005 | A2 | 9/2014 |
| WO | 2014197614 | A2 | 12/2014 |
| WO | 2015057766 | A1 | 4/2015 |
| WO | 2015077560 | A1 | 5/2015 |
| WO | 2015/168655 | A2 | 11/2015 |
| WO | 2016110824 | A1 | 7/2016 |
| WO | 2016123278 | A1 | 8/2016 |
| WO | 2016139590 | A1 | 9/2016 |
| WO | 2016139597 | A2 | 9/2016 |
| WO | 2016/178974 | A1 | 11/2016 |
| WO | 2016/187063 | A1 | 11/2016 |
| WO | 2016176065 | A1 | 11/2016 |
| WO | 2018089275 | A1 | 5/2018 |
| WO | 2018089285 | A1 | 5/2018 |
| WO | 2018089385 | A1 | 5/2018 |
| WO | 2018191547 | A1 | 10/2018 |
| WO | 2018213148 | A1 | 11/2018 |
| WO | 2018218236 | A1 | 11/2018 |
| WO | 2019/050576 | A1 | 3/2019 |
| WO | 2019/146026 | A1 | 8/2019 |
| WO | 2019199734 | A1 | 10/2019 |
| WO | 2020014149 | A1 | 1/2020 |
| WO | 2020069395 | A1 | 4/2020 |
| WO | 2020/109448 | A1 | 6/2020 |
| WO | 2020/113123 | A1 | 6/2020 |
| WO | 2021038041 | A1 | 3/2021 |
| WO | 2021050302 | A1 | 3/2021 |
| WO | 2021/077103 | A1 | 4/2021 |
| WO | 2021062023 | A1 | 4/2021 |
| WO | 2021081205 | A1 | 4/2021 |
| WO | 2021086793 | A1 | 5/2021 |
| WO | 2021/236950 | A1 | 11/2021 |
| WO | 2021226050 | A1 | 11/2021 |
| WO | 2022/031618 | A1 | 2/2022 |
| WO | 2022/094141 | A1 | 5/2022 |
| WO | 2022/133297 | A1 | 6/2022 |
| WO | 2022-140406 | A1 | 6/2022 |
| WO | 2022/140429 | A1 | 6/2022 |
| WO | 2022/217098 | A1 | 10/2022 |
| WO | 2023014994 | A1 | 2/2023 |
| WO | 2023/049498 | A1 | 3/2023 |
| WO | 2023049505 | A1 | 3/2023 |
| WO | 2023049511 | A1 | 3/2023 |
| WO | 2023049519 | A1 | 3/2023 |
| WO | 2023049522 | A1 | 3/2023 |
| WO | 2023/146792 | A1 | 8/2023 |

OTHER PUBLICATIONS

PCT/US2020/052536 filed Sep. 24, 2020 International Search Report and Written Opinion dated Dec. 4, 2020.

PCT/US2020/056364 filed Oct. 19, 2020 International Search Report and Written Opinion dated Jan. 19, 2021.

PCT/US2020/056864 filed Oct. 22, 2020 International Search Report and Written Opinion dated Jan. 14, 2021.

PCT/US2020/057202 filed Oct. 23, 2020 International Search Report and Written Opinion dated Jan. 21, 2021.

PCT/US2020/057397 filed Oct. 26, 2020 International Search Report and Written Opinion dated Mar. 10, 2021.

PCT/US2021/014700 filed Jan. 22, 2021 International Search Report and Written Opinion dated Jun. 29, 2021.

PCT/US2021/028018 filed Apr. 19, 2021 International Search Report and Written Opinion dated Sep. 13, 2021.

PCT/US2021/028683 filed Apr. 22, 2021 International Search Report and Written Opinion dated Sep. 16, 2021.

U.S. Appl. No. 15/008,628, filed Jan. 28, 2016 Final Office Action dated May 30, 2018.

U.S. Appl. No. 15/008,628, filed Jan. 28, 2016 Non-Final Office Action dated Jan. 25, 2019.

U.S. Appl. No. 15/008,628, filed Jan. 28, 2016 Non-Final Office Action dated Nov. 2, 2017.

U.S. Appl. No. 15/008,628, filed Jan. 28, 2016 Notice of Allowance dated May 15, 2019.

U.S. Appl. No. 16/398,020, filed Apr. 29, 2019 Non-Final Office Action dated May 11, 2021.

PCT/US2021/029183 filed Apr. 26, 2021 International Search Report and Written Opinion dated Sep. 24, 2021.

PCT/US2021/033443 filed May 20, 2021 International Search Report and Written Opinion dated Sep. 23, 2021.

PCT/US2021/039843 filed Jun. 30, 2021 International Search Report and Written Opinion dated Nov. 11, 2021.

PCT/US2021/044029 filed Jul. 30, 2021 International Search Report and Written Opinion dated Dec. 9, 2021.

PCT/US2021/039084 filed Jun. 25, 2021 International Search Report and Written Opinion dated Jan. 10, 2022.

U.S. Appl. No. 16/398,020, filed Apr. 29, 2019 Final Office Action dated Jan. 25, 2022.

U.S. Appl. No. 17/006,553, filed Aug. 28, 2020 Non-Final Office Action dated Mar. 16, 2022.

U.S. Appl. No. 17/077,728, filed Oct. 22, 2020 Non-Final Office Action dated Feb. 9, 2022.

PCT/US2021/064671 filed Dec. 21, 2021 International Search Report and Written Opinion dated May 27, 2022.

PCT/US2022/024085 filed Apr. 8, 2022 International Search Report and Wirtten Opinion dated Sep. 12, 2022.

U.S. Appl. No. 16/398,020, filed Apr. 29, 2019 Examiner's Answer dated Oct. 31, 2022.

U.S. Appl. No. 17/031,478, filed Sep. 24, 2020 Notice of Allowance dated Sep. 16, 2022.

(56) References Cited

OTHER PUBLICATIONS

U.S. Appl. No. 17/156,252, filed Jan. 22, 2021 Non-Final Office Action dated Oct. 25, 2022.
PCT/US2021/064642 filed Dec. 21, 2021 International Search Report and Written Opinion dated May 11, 2022.
PCT/US2021/044223 filed Aug. 2, 2021 International Search Report and Written Opinion dated Dec. 21, 2021.
PCT/US2021/048275 filed Aug. 30, 2021 International Search Report and Written Opinion dated Jan. 4, 2022.
PCT/US2021/064174 filed Dec. 17, 2021 International Search Report and Written Opinion dated May 18, 2022.
U.S. Appl. No. 17/031,478, filed Sep. 24, 2020 Non-Final Office Action dated May 11, 2022.
PCT/US2021/028018 filed Apr. 19, 2021 International Preliminary Report on Patentability dated Jun. 3, 2022.
PCT/US2021/057135 filed Oct. 28, 2021 International Preliminary Report on Patentability dated May 2, 2023.
PCT/US2021/057135 filed Oct. 28, 2021 International Search Report and Written Opinion dated Mar. 11, 2022.
PCT/US2022/039614 filed Aug. 5, 2022 International Search Report and Written Opinion dated Dec. 22, 2022.
PCT/US2022/044848 filed Sep. 27, 2022 International Search Report and Written Opinion dated Feb. 3, 2023.
PCT/US2022/044879 filed Sep. 27, 2022 International Search Report and Written Opinion dated Mar. 3, 2023.
PCT/US2022/044901 filed Sep. 27, 2022 International Search Report and Written Opinion dated Mar. 3, 2023.
PCT/US2022/044918 filed Sep. 27, 2022 International Search Report and Written Opinion dated Feb. 21, 2023.
PCT/US2022/044923 filed Sep. 27, 2022 International Search Report and Written Opinion dated Feb. 15, 2023.
U.S. Appl. No. 17/156,252, filed Jan. 22, 2021 Notice of Allowance dated Apr. 24, 2023.
U.S. Appl. No. 17/237,909, filed Apr. 22, 2021 Restriction Requirement dated Feb. 1, 2023.
U.S. Appl. No. 17/326,017, filed May 20, 2021 Non-Final Office Action dated Jan. 26, 2023.
U.S. Appl. No. 17/392,061, filed Aug. 2, 2021 Restriction Requirement dated Mar. 30, 2023.
U.S. Appl. No. 17/156,252, filed Jan. 22, 2021 Notice of Allowance dated Aug. 9, 2023.
U.S. Appl. No. 17/237,909, filed Apr. 22, 2021 Non-Final Office Action dated Jul. 27, 2023.
U.S. Appl. No. 17/240,591, filed Apr. 26, 2021 Non-Final Office Action dated Jun. 8, 2023.
U.S. Appl. No. 17/326,017, filed May 20, 2021 Notice of Allowance dated Jul. 3, 2023.
U.S. Appl. No. 17/358,504, filed Jun. 25, 2021 Restriction Requirement dated Jun. 7, 2023.
U.S. Appl. No. 17/360,694, filed Jun. 28, 2021 Restriction Requirement dated Jul. 20, 2023.
U.S. Appl. No. 17/392,061, filed Aug. 2, 2021 Non-Final Office Action dated Jul. 17, 2023.
PCT/US2023/011173 filed Jan. 19, 2023 International Search Report and Written Opinion dated May 22, 2023.
U.S. Appl. No. 16/398,020, filed Apr. 29, 2019 Board Decision dated Oct. 30, 2023.
U.S. Appl. No. 16/398,020, filed Apr. 29, 2019 Non-Final Office Action dated Jan. 18, 2024.
U.S. Appl. No. 17/234,611, filed Apr. 19, 2021 Restriction Requirement dated Jan. 18, 2024.
U.S. Appl. No. 17/237,909, filed Apr. 22, 2021 Notice of Allowance dated Oct. 27, 2023.
U.S. Appl. No. 17/240,591, filed Apr. 26, 2021 Advisory Action dated Feb. 22, 2024.
U.S. Appl. No. 17/240,591, filed Apr. 26, 2021 Final Office Action dated Dec. 6, 2023.
U.S. Appl. No. 17/358,504, filed Jun. 25, 2021 Non-Final Office Action dated Oct. 4, 2023.
U.S. Appl. No. 17/360,694, filed Jun. 28, 2021 Non-Final Office Action dated Feb. 14, 2024.
U.S. Appl. No. 17/360,694, filed Jun. 28, 2021 Non-Final Office Action dated Oct. 13, 2023.
U.S. Appl. No. 17/392,061, filed Aug. 2, 2021 Advisory Action dated Feb. 14, 2024.
U.S. Appl. No. 17/392,061, filed Aug. 2, 2021 Final Office Action dated Nov. 21, 2023.
U.S. Appl. No. 17/513,789, filed Oct. 28, 2021 Non-Final Office Action dated Jan. 9, 2024.
U.S. Appl. No. 17/513,789, filed Oct. 28, 2021 Restriction Requirement dated Oct. 3, 2023.
U.S. Appl. No. 17/557,924, filed Dec. 21, 2021 Final Office Action dated Feb. 29, 2024.
U.S. Appl. No. 17/557,924, filed Dec. 21, 2021 Non-Final Office Action dated Nov. 3, 2023.
U.S. Appl. No. 16/398,020, filed Apr. 29, 2019 Notice of Allowance dated May 20, 2024.
U.S. Appl. No. 17/234,611, filed Apr. 19, 2021 Non-Final Office Action dated Apr. 23, 2024.
U.S. Appl. No. 17/358,504, filed Jun. 25, 2021 Final Office Action dated Mar. 13, 2024.
U.S. Appl. No. 17/392,061, filed Aug. 2, 2021 Non-Final Office Action dated Apr. 23, 2024.
U.S. Appl. No. 17/554,978, filed Dec. 17, 2021 Non-Final Office Action dated Apr. 19, 2024.
U.S. Appl. No. 17/234,611, filed Apr. 19, 2021 Final Office Action dated Sep. 20, 2024.
U.S. Appl. No. 17/240,591, filed Apr. 26, 2021 Final Office Action dated Aug. 14, 2024.
U.S. Appl. No. 17/240,591, filed Apr. 26, 2021 Non-Final Office Action dated Jun. 4, 2024.
U.S. Appl. No. 17/358,504, filed Jun. 25, 2021 Notice of Allowance dated Jul. 17, 2024.
U.S. Appl. No. 17/513,789, filed Oct. 28, 2021 Final Office Action dated Jul. 9, 2024.
U.S. Appl. No. 17/554,978, filed Dec. 17, 2021 Notice of Allowance dated Jul. 24, 2024.
U.S. Appl. No. 17/557,924, filed Dec. 21, 2021 Non-Final Office Action dated Aug. 20, 2024.
U.S. Appl. No. 17/558,124, filed Dec. 21, 2021 Non-Final Office Action dated Sep. 20, 2024.
U.S. Appl. No. 17/234,611, filed Apr. 19, 2021 Examiner's Answer dated May 1, 2025.
U.S. Appl. No. 17/392,061, filed Aug. 2, 2021 Advisory Action dated Mar. 12, 2025.
U.S. Appl. No. 17/392,061, filed Aug. 2, 2021 Non-Final Office Action dated Apr. 5, 2025.
U.S. Appl. No. 17/558,124, filed Dec. 21, 2021 Notice of Allowance dated Mar. 7, 2025.
U.S. Appl. No. 17/461,619, filed Aug. 30, 2021 Advisory Action dated Aug. 14, 2025.
U.S. Appl. No. 17/461,619, filed Aug. 30, 2021 Final Office Action dated Jun. 2, 2025.
U.S. Appl. No. 17/716,675, filed Apr. 8, 2022 Restriction Requirement dated Jul. 2, 2025.
U.S. Appl. No. 17/882,388, filed Aug. 5, 2022 Non-Final Office Action dated Aug. 20, 2025.
U.S. Appl. No. 17/954,096, filed Sep. 27, 2022 Non-Final Office Action dated Aug. 26, 2025.
U.S. Appl. No. 17/954,132, filed Sep. 27, 2022 Non-Final Office Action dated Aug. 21, 2025.
U.S. Appl. No. 17/360,694, filed Jun. 28, 2021 Notice of Allowance dated Dec. 16, 2024.
U.S. Appl. No. 17/392,061, filed Aug. 2, 2021 Final Office Action dated Jan. 2, 2025.
U.S. Appl. No. 17/461,619, filed Aug. 30, 2021 Non-Final Office Action dated Feb. 11, 2025.
U.S. Appl. No. 17/461,619, filed Aug. 30, 2021 Restriction Requirement dated Dec. 6, 2024.
U.S. Appl. No. 17/513,789, filed Oct. 28, 2021 Notice of Allowance dated Jan. 3, 2025.

(56)                 References Cited

OTHER PUBLICATIONS

U.S. Appl. No. 17/557,924, filed Dec. 21, 2021 Notice of Allowance dated Dec. 11, 2024.
U.S. Appl. No. 17/392,061, filed Aug. 2, 2021 Notice of Allowance dated Oct. 27, 2025.
U.S. Appl. No. 17/461,619, filed Aug. 30, 2021 Non-Final Office Action dated Oct. 7, 2025.
U.S. Appl. No. 17/716,675, filed Apr. 8, 2022 Non-Final Office Action dated Sep. 11, 2025.
U.S. Appl. No. 17/953,663, filed Sep. 27, 2022 Restriction Requirement dated Oct. 3, 2025.
U.S. Appl. No. 17/953,860, filed Sep. 27, 2022 Restriction Requirement dated Oct. 22, 2025.
U.S. Appl. No. 17/953,959, filed Sep. 27, 2022 Restriction Requirement dated Oct. 22, 2025.
U.S. Appl. No. 18/099,185, filed Jan. 19, 2023 Non-Final Office Action dated Dec. 2, 2025.
U.S. Appl. No. 17/234,611, filed Apr. 19, 2021 Board Decision dated Jan. 23, 2026.
U.S. Appl. No. 17/882,388, filed Aug. 5, 2022 Final Office Action dated Jan. 12, 2026.
U.S. Appl. No. 17/953,663, filed Sep. 27, 2022 Non-Final Office Action dated Jan. 22, 2026.
U.S. Appl. No. 17/953,860, filed Sep. 27, 2022 Non-Final Office Action dated Jan. 29, 2026.
U.S. Appl. No. 17/954,096, filed Sep. 27, 2022 Final Office Action dated Feb. 10, 2026.
U.S. Appl. No. 18/372,610, filed Sep. 25, 2023 Notice of Allowance dated Dec. 16, 2025.
U.S. Appl. No. 18/383,814, filed Oct. 25, 2023 Restriction Requirement dated Jan. 22, 2026.

* cited by examiner

162

200

224

222

214

226

220

216

218

214

202

222

PROXIMAL

DISTAL

SECTION A

SECTION B

SECTION C

SECTION D OR E

TWO-PIECE RAPIDLY INSERTABLE CENTRAL CATHETERS, INTRODUCERS THEREFOR, AND METHODS THEREOF

PRIORITY

This application claims the benefit of priority to U.S. Provisional Patent Application No. 63/059,798, filed Jul. 31, 2020, which is incorporated by reference in its entirety into this application.

BACKGROUND

Existing catheters are manufactured as whole ready-to-use catheters. Such catheters can have lengths ranging from 30 to 40 cm as measured from the proximal end to the distal end of any such catheter. Rapidly insertable central catheters ("RICCs") currently under development are introduced over introducer needles. Introduction of the RICCs over 30-40 cm introducer needles could be cumbersome for clinicians. In addition, it could be difficult to timely discern whether blood flashback has occurred and access to a blood-vessel lumen established during any given RICC introduction with a 30-40 cm introducer needle. As such, the RICCs generally include distal introducing apertures designed for introduction of the RICCs over shorter introducer needles. However, it would be beneficial to eliminate the introducing apertures as they become, in effect, artifacts after introduction of the RICCs.

Disclosed herein are two-piece RICCs, introducers therefor, and methods thereof that address the foregoing.

SUMMARY

Disclosed herein is a RICC system including, in some embodiments, a distal catheter piece of a RICC and an introducer configured to combine in an introducer assembly having a ready-to-deploy state. The introducer assembly is configured to be actuated with a single finger of a hand while the introducer is held between a thumb and another finger or fingers of the hand. The distal catheter piece includes a distal catheter-hub piece of a two-piece catheter hub and a catheter tube coupled to the distal catheter-hub piece by a proximal portion of the catheter tube. The catheter tube includes one or more catheter-tube lumens. The introducer includes a catheter-advancement hub, an introducer needle, a syringe, and an introducer housing. The catheter-advancement hub includes a manifold and a side arm coupled to a proximal portion of the distal catheter-hub piece in the ready-to-deploy state of the introducer assembly. The introducer needle has a needle shaft extending through both the manifold and a distal end of the distal catheter piece in the ready-to-deploy state of the introducer assembly. The syringe includes a barrel having a distal portion terminating in a syringe tip. The syringe is fluidly coupled to the introducer needle. The introducer housing is over the syringe tip, the manifold, and the proximal portion of the distal catheter piece in the ready-to-deploy state of the introducer assembly. The introducer housing is configured to provide column strength to the catheter tube during a venipuncture with the introducer needle. The introducer housing is also configured to longitudinally split allowing the distal catheter piece to be removed from the introducer housing after the venipuncture.

In some embodiments, the introducer housing includes a lock in a distal portion of the introducer housing. The lock includes a hook in a slidable piece of the introducer housing and a latch in a stationary piece of the introducer housing. The hook and latch are configured to lock the slidable piece and the stationary piece together in the ready-to-deploy state of the introducer assembly.

In some embodiments, the stationary piece of the introducer housing includes a channel. The channel includes the latch in a proximal portion of the channel and a ramp in a distal portion of the channel. A combination of the hook and the ramp are configured to push the slidable piece of the introducer housing away from the stationary piece when a distal face of the hook engages a proximal face of the ramp while distally advancing the slidable piece relative to the stationary piece.

In some embodiments, the introducer housing includes a sliding hinge in a proximal portion of the introducer housing. The sliding hinge includes a captive tab of the slidable piece of the introducer housing and a track of the stationary piece of the introducer housing. The captive tab is captively but slidably disposed in the track allowing the slidable piece to be distally advanced relative to the stationary piece without separating the slidable piece from the stationary piece in the proximal portion of the introducer housing.

In some embodiments, a proximal portion of the captive tab inboard of an exterior surface of the introducer housing is radiused. The captive tab being radiused facilitates splitting the slidable piece of the introducer housing from the stationary piece of the introducer housing in the distal portion of the introducer housing.

In some embodiments, the proximal portion of the introducer housing includes a longitudinal cutout. The cutout is configured to provide a path for the side arm of the catheter-advancement hub while distally advancing the catheter-advancement hub within the introducer housing.

In some embodiments, the manifold includes one or more manifold lumens equal in number to the one-or-more catheter-tube lumens. The one-or-more manifold lumens are fluidly connected to the one-or-more catheter-tube lumens in the ready-to-deploy state of the introducer assembly.

In some embodiments, the side arm of the catheter-advancement hub includes a side-arm lumen fluidly coupled to the one-or-more manifold lumens. A combination of the side-are lumen and the one-or-more manifold lumens is for simultaneously priming each lumen of the one-or-more catheter-tube lumens before inserting the catheter tube into a blood-vessel lumen of the patient.

In some embodiments, the catheter-advancement hub further includes a catheter-advancement push tab extending from the side arm. The catheter-advancement push tab is configured for distally advancing the catheter-advancement hub with the single finger of the hand while holding the syringe around the distal portion of the barrel between the thumb and the other finger or fingers of the hand.

In some embodiments, the RICC system further includes a proximal catheter piece of the RICC. The proximal catheter piece includes a proximal catheter-hub piece of the two-piece catheter hub and one or more extension legs. The one-or-more extension legs respectively include one or more extension-leg lumens. Each extension leg of the one-or-more extension legs is coupled to the proximal catheter-hub piece by a distal portion of the extension leg. The RICC has a connected state in which the proximal catheter-hub piece is connected to the distal catheter-hub piece. In the connected state of the RICC, the one-or-more extension-leg lumens are respectively fluidly coupled to the one-or-more catheter-tube lumens across the two-piece catheter hub.

In some embodiments, the RICC includes a set of three lumens in the connected state of the RICC. The set of three lumens includes a primary lumen, a secondary lumen, and a tertiary lumen.

In some embodiments, the primary lumen has a primary-lumen aperture in a distal end of the two-piece catheter, the secondary lumen has a secondary-lumen aperture in a side of the catheter tube proximal of the primary-lumen aperture, and the tertiary lumen has a tertiary-lumen aperture in the side of the catheter tube proximal of the secondary-lumen aperture.

In some embodiments, the catheter tube further includes a first section formed of a first material having a first durometer a second section formed of a second material having a second durometer less than the first durometer. The catheter tube thereby configured with both column strength for inserting the catheter tub into the patient and compliance for advancing the catheter tube through a vasculature of the patient.

In some embodiments, the introducer further includes a syringe housing around the barrel of the syringe having a distal portion and a proximal portion. The proximal portion of the syringe housing is either integral with or coupled to a proximal portion of a plunger disposed in the barrel. Whether the proximal portion of the syringe housing is integral with or coupled to the proximal portion of the plunger, proximally sliding the syringe housing relative to the barrel withdraws the plunger from the barrel.

In some embodiments, the syringe further includes a plunger-withdrawal push tab proximally extending over the barrel from the distal portion of the barrel to which the plunger-withdrawal push tab is coupled. The plunger-withdrawal push tab is configured for pushing against with the single finger of the hand while holding the syringe around the distal portion of the barrel between the thumb and the other finger or fingers of the hand to proximally slide the syringe housing relative to the barrel and withdraw the plunger from the barrel.

In some embodiments, the introducer further includes an access guidewire disposed in an access-guidewire lumen formed of at least a plunger lumen of the plunger and a needle lumen of the introducer needle. The access guidewire has a length sufficient for extension of the access guidewire through the distal end of the distal catheter piece.

In some embodiments, the introducer further includes a slider distally extending over the barrel from the syringe housing. The slider is configured for actuating the access guidewire with the single finger of the hand while holding the syringe around the distal portion of the barrel between the thumb and the other finger or fingers of the hand. The slider includes an extension extending through a longitudinal slot in each of the barrel and the plunger into the access-guidewire lumen where the extension is coupled to the access guidewire.

Also disclosed is an introducer configured to couple to a distal catheter piece of a RICC in an introducer assembly. The introducer includes a catheter-advancement hub, an introducer needle, a syringe, and an introducer housing. The catheter-advancement hub includes a manifold and a side arm configured to couple to the distal catheter piece in the introducer assembly. The introducer needle has a needle shaft extending through both the manifold and a distal end of the distal catheter piece in a ready-to-deploy state of the introducer assembly. The syringe is fluidly coupled to the introducer needle. The syringe includes a barrel having a distal portion terminating in a syringe tip. The syringe is configured to be held around the distal portion of the barrel between a thumb and another finger or fingers of a hand while reserving a single finger for actuating the introducer. The introducer housing is over the syringe tip, the manifold, and the proximal portion of the distal catheter piece in the ready-to-deploy state of the introducer assembly. The introducer housing is configured to provide column strength to a catheter tube of the distal catheter piece during a venipuncture with the introducer needle. The introducer housing is also configured to longitudinally split allowing the distal catheter piece to be removed from the introducer housing after the venipuncture.

In some embodiments, the introducer housing includes a lock in a distal portion of the introducer housing. The lock includes a hook in a slidable piece of the introducer housing and a latch in a stationary piece of the introducer housing. The hook and latch are configured to lock the slidable piece and the stationary piece together.

In some embodiments, the stationary piece of the introducer housing includes a channel. The channel includes the latch in a proximal portion of the channel and a ramp in a distal portion of the channel. A combination of the hook and the ramp are configured to push the slidable piece of the introducer housing away from the stationary piece when a distal face of the hook engages a proximal face of the ramp while distally advancing the slidable piece relative to the stationary piece.

In some embodiments, the introducer housing includes a sliding hinge in a proximal portion of the introducer housing. The sliding hinge includes a captive tab of the slidable piece of the introducer housing and a track of the stationary piece of the introducer housing. The captive tab is captively but slidably disposed in the track allowing the slidable piece to be distally advanced relative to the stationary piece without separating the slidable piece from the stationary piece in the proximal portion of the introducer housing.

In some embodiments, a proximal portion of the captive tab inboard of an exterior surface of the introducer housing is radiused. The captive tab being radiused facilitates splitting the slidable piece of the introducer housing from the stationary piece of the introducer housing in the distal portion of the introducer housing.

In some embodiments, the proximal portion of the introducer housing includes a longitudinal cutout. The cutout is configured to provide a path for the side arm of the catheter-advancement hub while distally advancing the catheter-advancement hub within the introducer housing.

In some embodiments, the side arm of the catheter-advancement hub includes a side-arm lumen fluidly coupled to one or more manifold lumens. A combination of the side-are lumen and the one-or-more manifold lumens is for simultaneously priming each lumen of one or more lumens of the distal catheter piece of the RICC in the ready-to-deploy state of the introducer assembly.

In some embodiments, the catheter-advancement hub further includes a catheter-advancement push tab extending from the side arm. The catheter-advancement push tab is configured for distally advancing the catheter-advancement hub with the single finger of the hand while holding the syringe around the distal portion of the barrel between the thumb and the other finger or fingers of the hand.

In some embodiments, the introducer further includes a syringe housing around the barrel of the syringe having a distal portion and a proximal portion. The proximal portion of the syringe housing is either integral with or coupled to a proximal portion of a plunger disposed in the barrel. Whether the proximal portion of the syringe housing is integral with or coupled to the proximal portion of the plunger, proximally sliding the syringe housing relative to the barrel withdraws the plunger from the barrel.

In some embodiments, the syringe further includes a plunger-withdrawal push tab proximally extending over the barrel from the distal portion of the barrel to which the plunger-withdrawal push tab is coupled. The plunger-withdrawal push tab is configured for pushing against with the single finger of the hand while holding the syringe around the distal portion of the barrel between the thumb and the other finger or fingers of the hand to proximally slide the syringe housing relative to the barrel and withdraw the plunger from the barrel.

In some embodiments, the introducer further includes an access guidewire disposed in an access-guidewire lumen formed of at least a plunger lumen of the plunger and a needle lumen of the introducer needle. The access guidewire has a length sufficient for extension of the access guidewire through the distal end of the distal catheter piece in the ready-to-deploy state of the introducer assembly.

In some embodiments, the introducer further includes a slider distally extending over the barrel from the syringe housing. The slider is configured for actuating the access guidewire with the single finger of the hand while holding the syringe around the distal portion of the barrel between the thumb and the other finger or fingers of the hand. The slider includes an extension extending through a longitudinal slot in each of the barrel and the plunger into the access-guidewire lumen where the extension is coupled to the access guidewire.

Also disclosed is a method of a RICC system. The method includes, in some embodiments, a RICC system-obtaining step, a needle tract-establishing step, a first RICC-advancing step, an introducer housing-splitting step, and an introducer-removing step. The RICC system-obtaining step includes obtaining the RICC system. The RICC system includes a proximal catheter piece of a RICC and an introducer assembly. The introducer assembly includes an introducer and a distal catheter piece of the RICC partially disposed in an introducer housing of the introducer. The needle tract-establishing step includes establishing a needle tract from an area of skin to a blood-vessel lumen of a patient with an introducer needle of the introducer. The introducer needle has a needle shaft extending through a distal end of the distal catheter piece in a ready-to-deploy state of the introducer assembly. The needle tract-establishing step is performed holding a distal portion of a syringe of the introducer between a thumb and another finger or fingers of a hand while keeping at least a single finger of the hand readily available for actuating the introducer assembly. The first RICC-advancing step includes advancing a distal portion of a first section of a catheter tube of the distal catheter piece into the blood-vessel lumen over the needle shaft. The introducer housing-splitting step includes splitting the introducer housing along a length of the introducer housing. The introducer-removing step includes removing the distal catheter piece from the introducer housing leaving the distal portion of the first section of the catheter tube in place in the blood-vessel lumen.

In some embodiments, the method further includes a blood-aspirating step. The blood-aspirating step includes aspirating blood with the syringe to confirm a needle tip of the introducer needle is disposed in the blood-vessel lumen before the introducer-removing step. The blood-aspirating step includes pushing a plunger-withdrawal push tab with the single finger of the hand while holding the distal portion of the syringe by a syringe housing over a barrel of the syringe between the thumb and the other finger or fingers of the hand. The plunger-withdrawal push tab extends over the barrel from the distal portion of the syringe such that pushing the plunger-withdrawal tab while holding the distal portion of the syringe by the syringe housing proximally slides the syringe housing relative to the barrel and withdraws a syringe housing-connected plunger from the barrel.

In some embodiments, the first RICC-advancing step includes pushing a catheter-advancement push tab with the single finger of the hand while holding the distal portion of the syringe between the thumb and the other finger or fingers of the hand. The catheter-advancement push tab is part of a catheter-advancement hub coupled to a proximal portion of the distal catheter piece in the ready-to-deploy state of the introducer assembly.

In some embodiments, pushing the catheter-advancement push tab advances a side arm of the catheter-advancement hub along a path provided by a longitudinal cutout of the introducer housing.

In some embodiments, the method further includes priming step. The priming step includes priming the distal catheter piece with a common syringe through a side arm of the catheter-advancement hub before the first RICC-advancing step. The side arm has a side-arm lumen fluidly coupled to one or more manifold lumens for simultaneously priming each lumen of a respective one or more lumens of the distal catheter piece.

In some embodiments, the introducer housing-splitting step includes unlocking a lock in a distal portion of the introducer housing by distally sliding a slidable piece of the introducer housing relative to a stationary piece of the introducer housing. The unlocking of the lock includes separating a hook of a slidable piece and a latch of the stationary piece with the sliding of the slidable piece relative to the stationary piece.

In some embodiments, the stationary piece of the introducer housing includes a channel including the latch in a proximal portion of the channel and a ramp in a distal portion of the channel. The sliding of the slidable piece relative to the stationary piece causes a distal face of the hook to engage a proximal face of the ramp and split the introducer housing along the length of introducer housing.

In some embodiments, the method further includes an access guidewire-advancing step. The access guidewire-advancing step includes advancing an access guidewire disposed in an access-guidewire lumen into the blood-vessel lumen beyond the distal end of the distal catheter piece. The access-guidewire lumen is formed of at least a plunger lumen of the syringe and a needle lumen of the introducer needle. In addition, a slider is coupled to the access guidewire such that distally advancing the slider with the single finger while holding the distal portion of the syringe housing between the thumb and the other finger or fingers of the hand advances the access guidewire into the blood-vessel lumen. The access guidewire-advancing step is performed before the first RICC-advancing step.

In some embodiments, the method further includes a catheter hub-clipping step. The catheter hub-clipping step includes clipping together a proximal catheter-hub piece of the proximal catheter piece and a proximal catheter-hub piece of the distal catheter piece. The catheter hub-clipping step respectively connects one or more extension-leg lumens of one or more extension legs coupled to the proximal catheter-hub piece to one or more catheter-tube lumens of the catheter tube, thereby forming the RICC.

In some embodiments, the method further includes a maneuver guidewire-advancing step. The maneuver guidewire-advancing step includes advancing a maneuver guidewire into the blood-vessel lumen to a target location in a vasculature of the patient by way of a primary lumen of the RICC having a primary-lumen aperture in the distal end of the distal catheter piece.

In some embodiments, the method further includes a second RICC-advancing step and a maneuver guidewire-removing step. The second RICC-advancing step includes advancing a remainder of the distal portion of the first section of the catheter tube into the blood-vessel lumen up to a proximal portion of a second section of the catheter tube using the maneuver guidewire as a guide. The second RICC-advancing step is stopped with respect to the advancing when the distal end of the distal catheter piece arrives at the target location. The maneuver guidewire-removing step includes withdrawing the maneuver guidewire and leaving the catheter tube in place in the patient.

These and other features of the concepts provided herein will become more apparent to those of skill in the art in view of the accompanying drawings and following description, which describe particular embodiments of such concepts in greater detail.

DRAWINGS

DESCRIPTION

Figure 1:
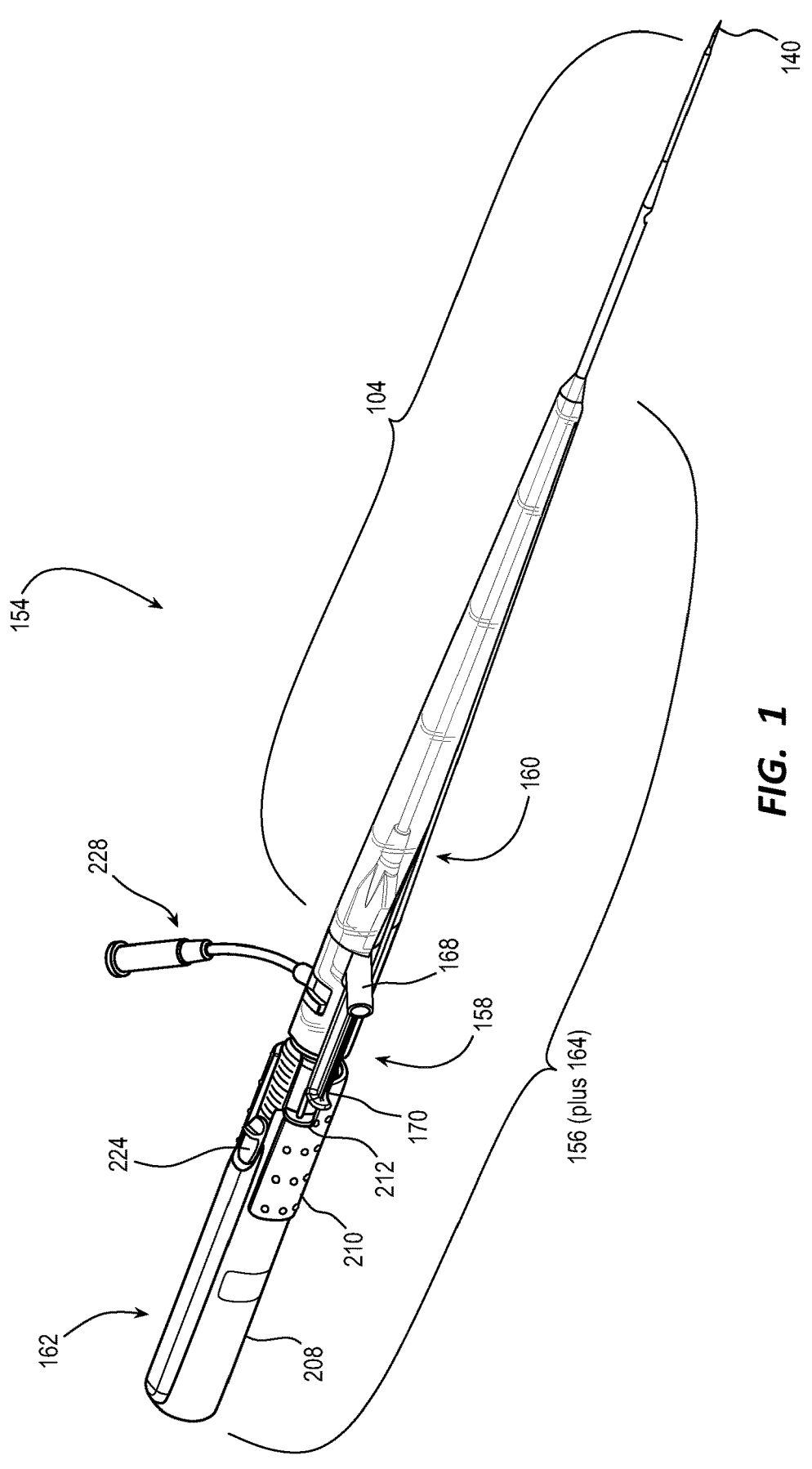
FIG. 1 illustrates a first oblique view of an introducer assembly including an introducer and a distal catheter piece of a two-piece RICC in accordance with some embodiments.
Figure 2:
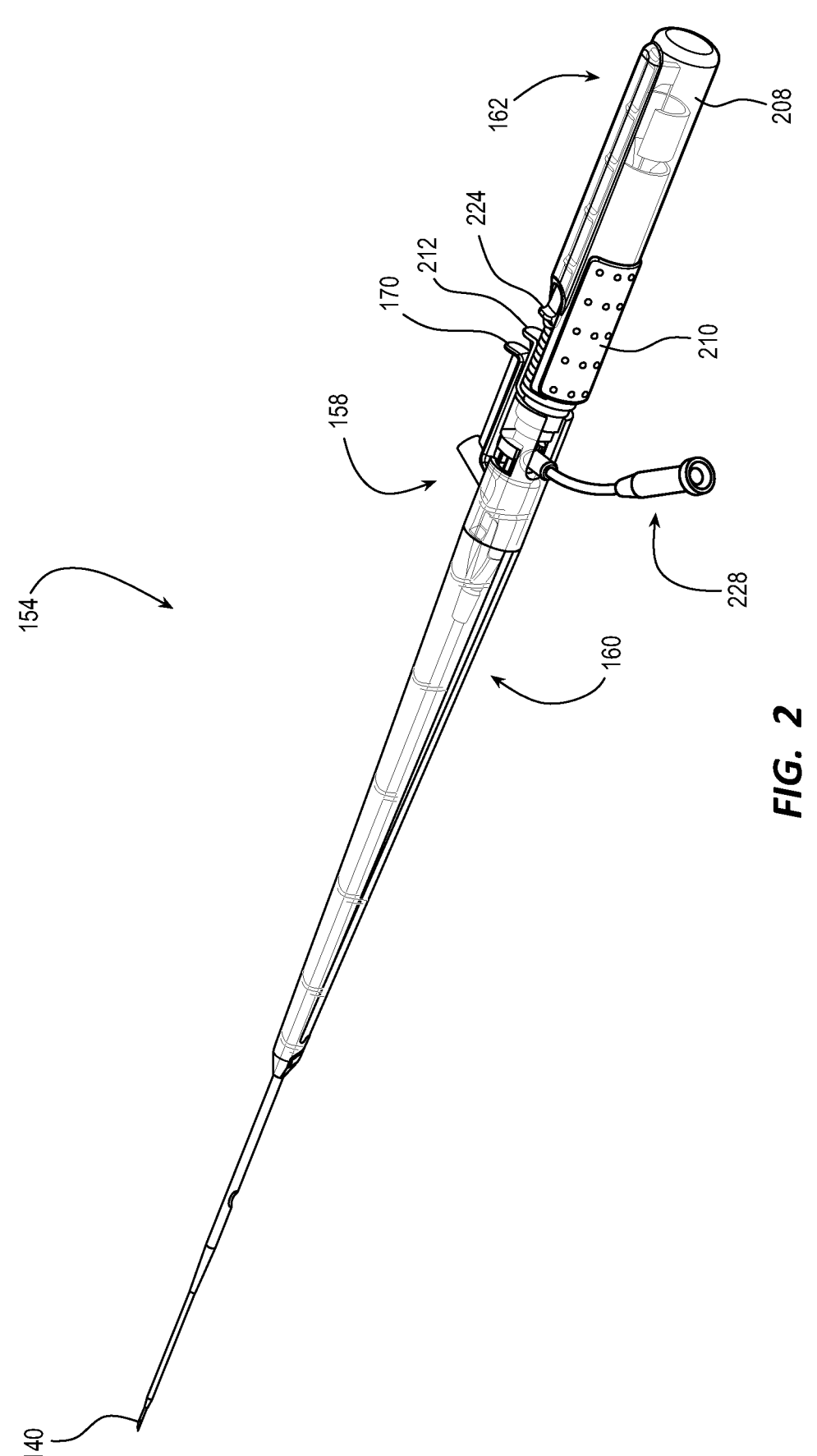
FIG. 2 illustrates a second oblique view of the introducer assembly in accordance with some embodiments.
Figure 3:
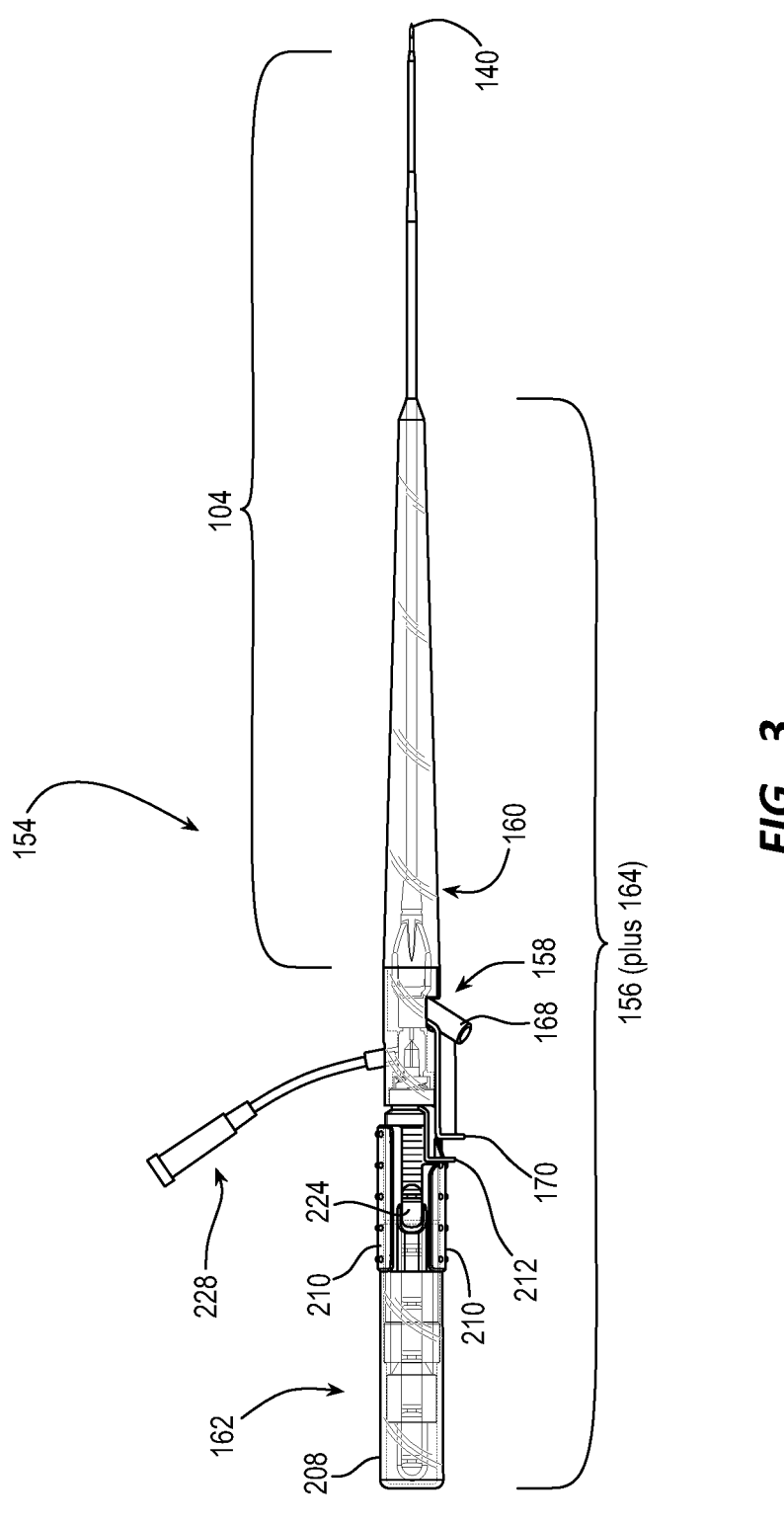
FIG. 3 illustrates a top view of the introducer assembly in accordance with some embodiments.
Figure 4:
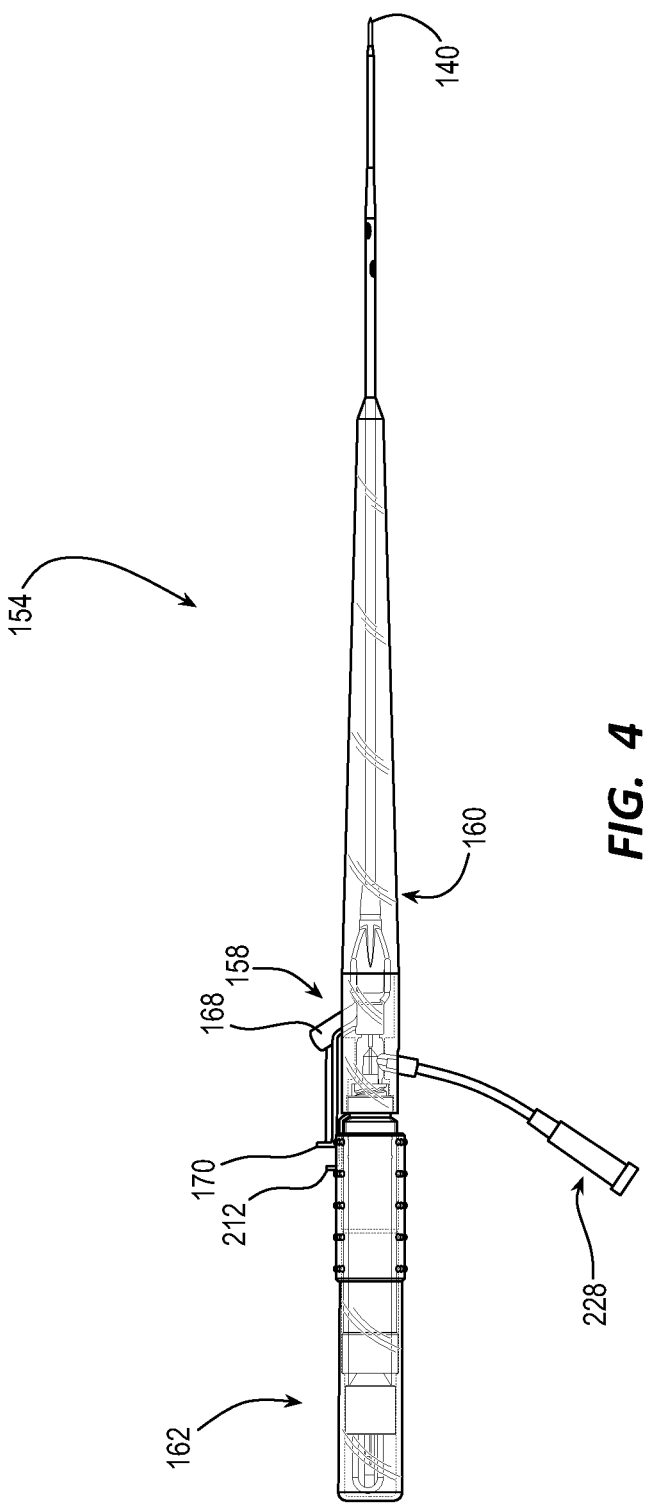
FIG. 4 illustrates a bottom view of the introducer assembly in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

As set forth above, RICCs generally include distal introducing apertures designed for introduction of the RICCs over shorter introducer needles. However, it would be beneficial to eliminate the introducing apertures as they become, in effect, artifacts after introduction of the RICCs.

Disclosed herein are two-piece RICCs, introducers therefor, and methods thereof that address the foregoing. For context, description for the RICCs is presented first. The description for the RICCs is followed by description for the introducers, which description is sometimes presented in the context of introducer assemblies in view of the interrelatedness of the introducer and the RICCs. Following description of the RICCs and the introducers, the methods are presented for at least using RICC systems including the foregoing RICCs and introducers.

Rapidly Insertable Central Catheters

Figure 13:
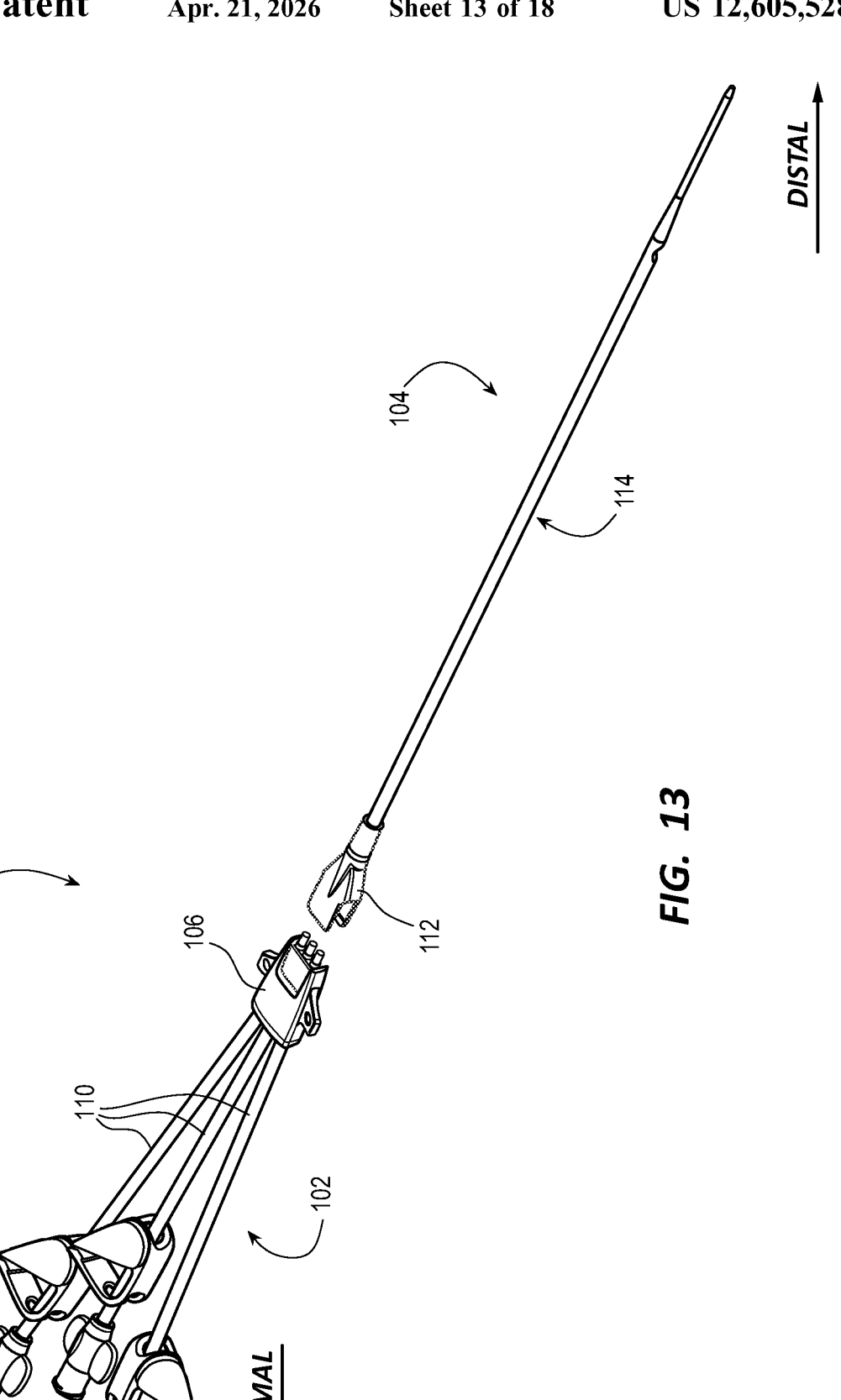
FIG. 13 illustrates the two-piece RICC in an unconnected state in accordance with some embodiments.
Figure 14:
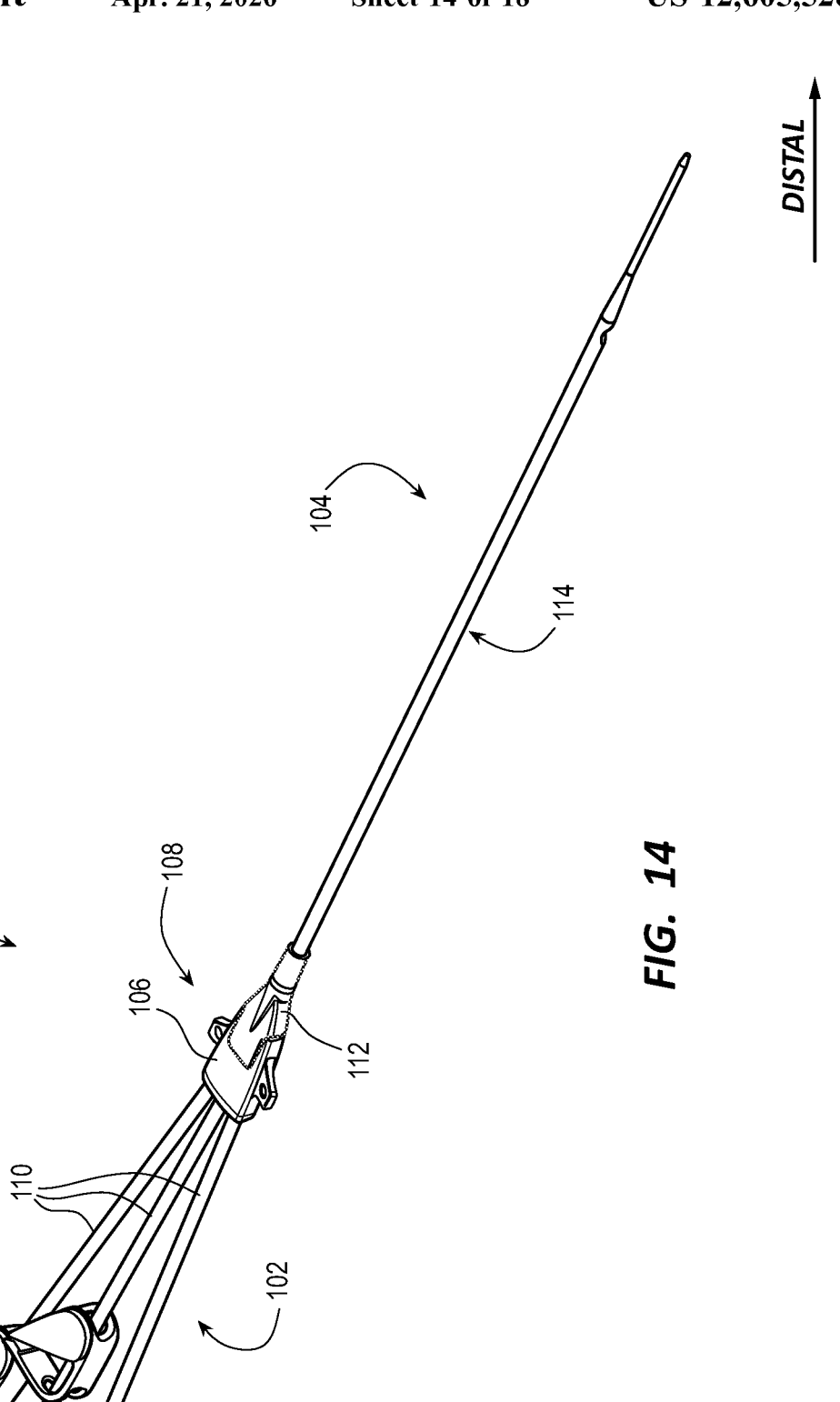
FIG. 14 illustrates the two-piece RICC in a connected state in accordance with some embodiments.

FIGS. 13 and 14 illustrate a two-piece RICC 100 in an unconnected state and a connected state in accordance with some embodiments.

As shown, the two-piece RICC 100 includes two pieces including a proximal catheter piece 102 and a distal catheter piece 104. It should be understood the RICC 100 can include different pieces or additional pieces to those in the illustrated embodiments. Indeed, the "two pieces" of the two-piece RICC 100 generally refer to at least two pieces resulting from transversely dividing such a RICC at some point along its length, in this case, at the two-piece catheter hub 108 set forth below.

The proximal catheter piece 102 includes a proximal catheter-hub piece 106 of a two-piece catheter hub 108 and one or more extension legs 110. The distal catheter piece 104 includes a distal catheter-hub piece 112 of the two-piece catheter hub 108 and a catheter tube 114. Description for the two-piece catheter hub 108 is presented first followed by description for the catheter tube 114, the one-or-more extension legs 110, and other aspects of the RICC 100.

Figure 15:
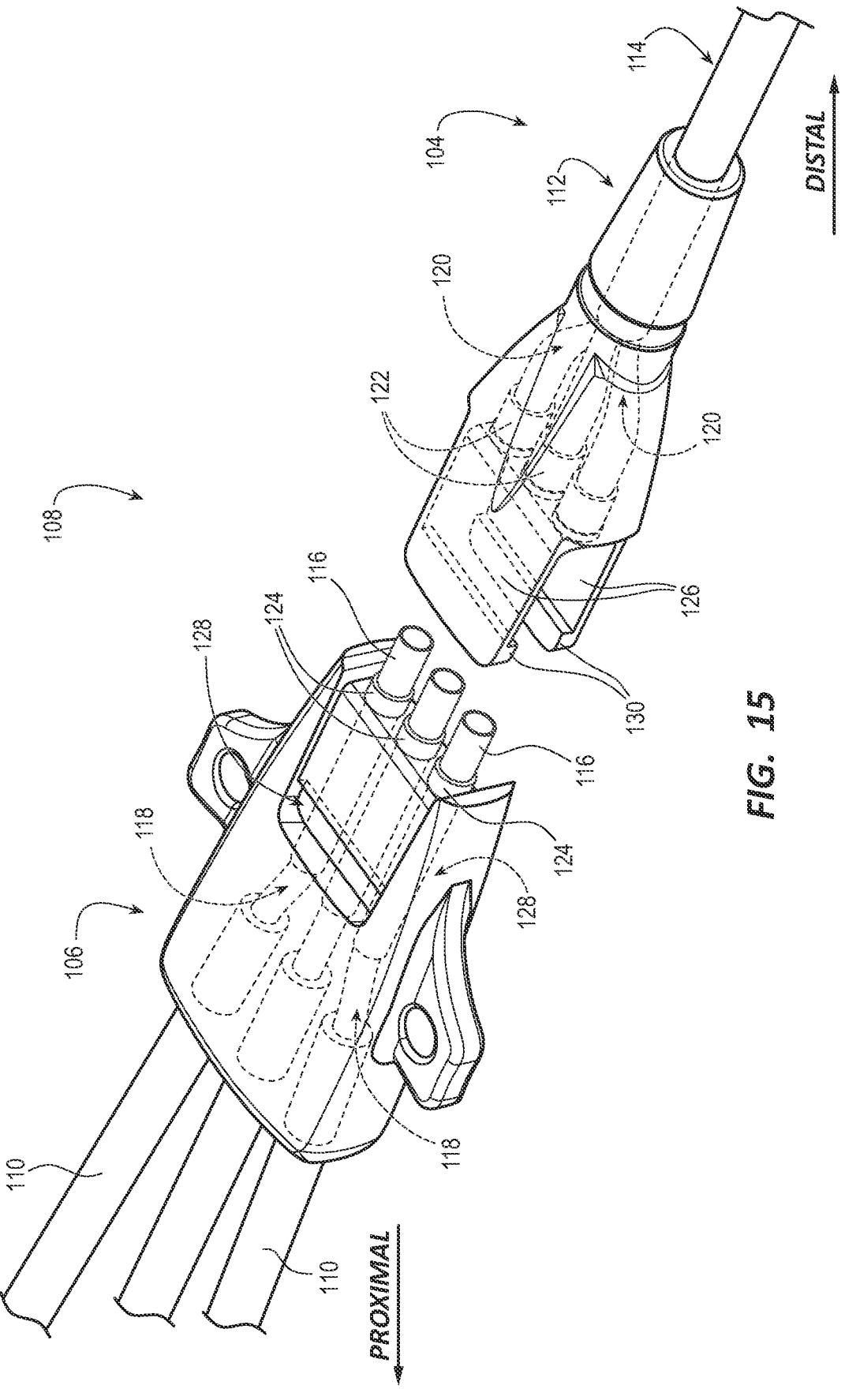
FIG. 15 illustrates a proximal catheter-hub piece and the distal catheter-hub piece of a two-piece catheter hub in the unconnected state of the RICC in accordance with some embodiments.
Figure 16:
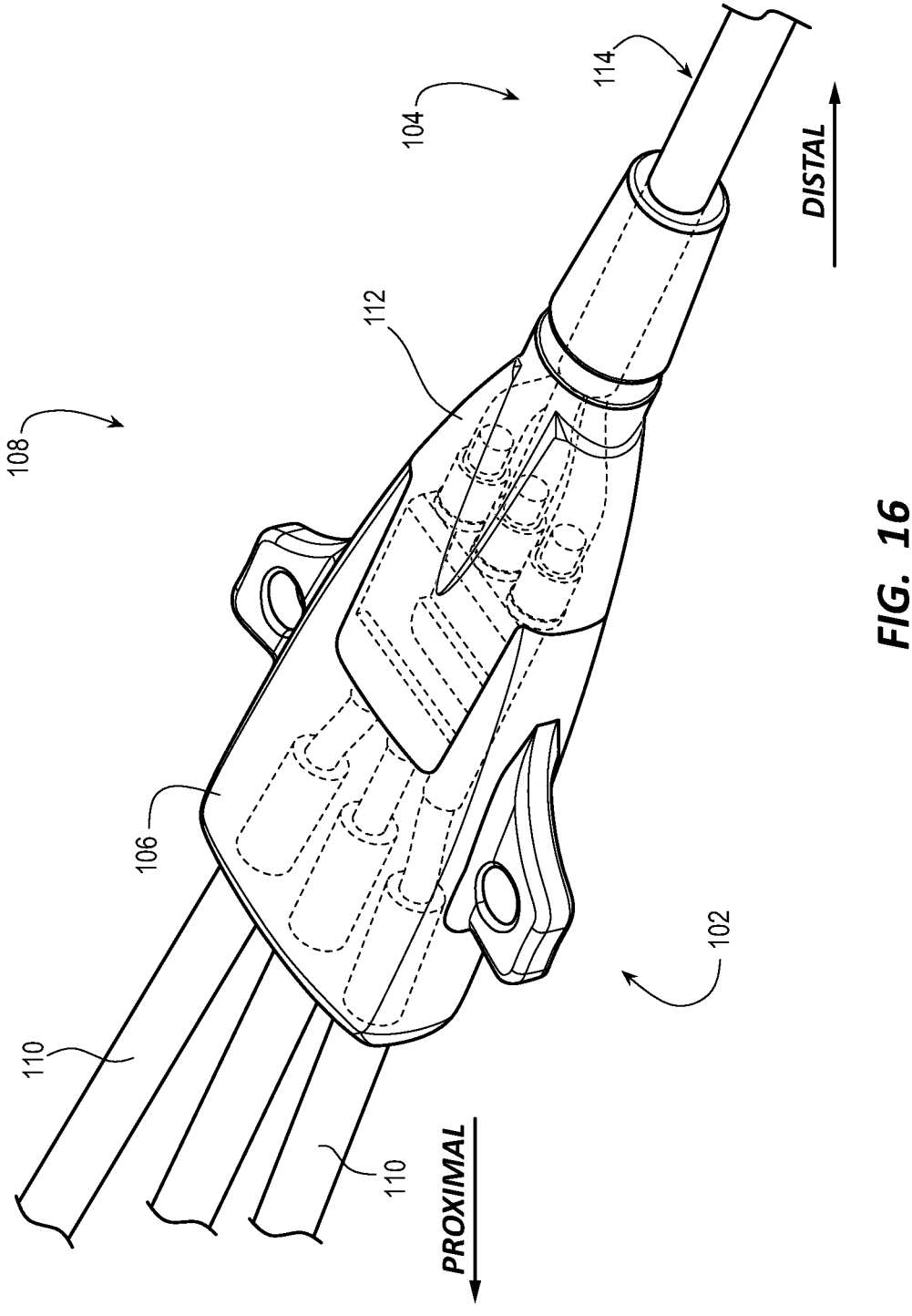
FIG. 16 illustrates the proximal catheter-hub piece and the distal catheter-hub piece in the connected state of the RICC in accordance with some embodiments.

FIGS. 15 and 16 illustrate the proximal catheter-hub piece 106 and the distal catheter-hub piece 112 of the two-piece catheter hub 108 in the unconnected state and the connected state of the RICC 100 in accordance with some embodiments.

The proximal catheter-hub piece 106 of the two-piece catheter hub 108 includes one or more rigid tubes 116 (e.g., metal tubes) respectively disposed in one or more proximal catheter-hub lumens 118, thereby effectively extending the one-or-more proximal catheter-hub lumens 118 in connectors. The proximal catheter-hub piece 106 can be molded over the one-or-more rigid tubes 116 during manufacturing such that the one-or-more rigid tubes 116 extend from a distal end of the proximal catheter-hub piece 106. Alternatively, the one-or-more rigid tubes 116 are inserted into the one-or-more proximal catheter-hub lumens 118 during manufacturing such that the one-or-more rigid tubes 116 extend from the distal end of the proximal catheter-hub piece 106.

The distal catheter-hub piece 112 of the two-piece catheter hub 108 includes one or more distal catheter-hub lumens 120 including one or more mechanical gaskets 122 respectively disposed therein. The one-or-more mechanical gaskets 122 are configured to sit between abluminal surfaces of the one-or-more rigid tubes 116 and luminal surfaces of the one-or-more distal catheter-hub lumens 120 in the connected state of the RICC 100. The one-or-more mechanical gaskets 122 include, but are not limited to, 'O'-rings or cylinders. The one-or-more mechanical gaskets 122 can be formed of a compressible polymeric material such as a silicone. Use of a compressible polymeric material such as silicone is advantageous in that axial compression of the one-or-more mechanical gaskets 122 by compression annuli 124 when inserting the one-or-more rigid tubes 116 into the one-or-more distal catheter-hub lumens 120 forces the one-or-more mechanical gaskets 122 to radially expand in the limited space between the abluminal surfaces of the one-or-more rigid tubes 116 and the luminal surfaces of the one-or-more distal catheter-hub lumens 120, thereby creating one or more fluid-tight luminal seals between the proximal catheter-hub piece 106 and the distal catheter-hub piece 112 of the two-piece catheter hub 108 and respectively continuing the one-or-more proximal catheter-hub lumens 118 into the one-or-more distal catheter-hub lumens 120.

In an alternative to the foregoing, the distal catheter-hub piece 112 can instead include the one-or-more rigid tubes 116 respectively disposed in the one-or-more distal catheter-hub lumens 120. Likewise, the proximal catheter-hub piece 106 can instead include the one-or-more mechanical gaskets 122 respectively disposed in the one-or-more proximal catheter-hub lumens 118. It should be understood the foregoing description for the one-or-more rigid tubes 116, the one-or-more mechanical gaskets 122, and the like for the illustrated embodiments of the proximal catheter-hub piece 106 and the distal catheter-hub piece 112 apply to the one-or-more rigid tubes 116 when part of the distal catheter-hub piece 112, the one-or-more mechanical gaskets 122 when part of the proximal catheter-hub piece 106, and the like.

Continuing with the illustrated embodiments of the proximal catheter-hub piece 106 and the distal catheter-hub piece 112, the proximal catheter-hub piece 106 and the distal catheter-hub piece 112 include complementary connectors of a connection system configured to securely and, in some embodiments, irreversibly connect the proximal catheter-hub piece 106 and the distal catheter-hub piece 112 in the connected state of the RICC 100. "Irreversibly" connecting the proximal catheter-hub piece 106 and the distal catheter-hub piece 112 in this context should be understood to mean the proximal catheter-hub piece 106 and the distal catheter-hub piece 112 cannot be disconnected without tools or damage to the proximal catheter-hub piece 106 or the distal catheter-hub piece 112.

As to the connection system, the distal catheter-hub piece 112 can include an integral clip molded together with the distal catheter-hub piece 112 itself, the integral clip having tabbed arms 126 proximally extending from the distal catheter-hub piece 112. The proximal catheter-hub piece 106 can include complementary receivers such as surface recesses 128 configured to seat both the tabbed arms 126 and tabs 130 of the tabbed arms 126 therein in the connected state of the RICC 100. As best shown in FIG. 15, the tabbed arms 126 can extend from major sides of the distal catheter-hub piece 112 and the surface recesses 128 can be in major surfaces of the proximal catheter-hub piece 106. However, the tabbed arms 126 can alternatively extend from minor sides of the distal catheter-hub piece 112 and the surface recesses 128 can be in minor surfaces of the proximal catheter-hub piece 106. Due to greater design space across a width of the two-piece catheter hub 108, the complementary receivers can instead be longitudinal cavities inboard of the minor surfaces of the proximal catheter-hub piece 106 into which the tabbed arms 126 extending from the minor sides of the distal catheter-hub piece 112 are configured to insert, which is similar to that of common plastic buckles on backpacks and the like.

In an alternative to the foregoing, the proximal catheter-hub piece 106 can instead include the integral clip having the tabbed arms 126. Indeed, provided the one-or-more rigid tubes 116 are also disposed in the one-or-more proximal catheter-hub lumens 118 of the proximal catheter-hub piece 106, the integral clip effectively protects the one-or-more rigid tubes 116 from inadvertent damage. Likewise, the distal catheter-hub piece 112 can instead include the complementary receivers including the surface recesses 128 configured to seat the tabbed arms 126. It should be understood the foregoing description for the tabbed arms 126, the complementary receivers, and the like for the illustrated embodiments of the proximal catheter-hub piece 106 and the distal catheter-hub piece 112 apply to the tabbed arms 126 when part of the proximal catheter-hub piece 106, the complementary receivers when part of the distal catheter-hub piece 112, and the like.

Figure 17:
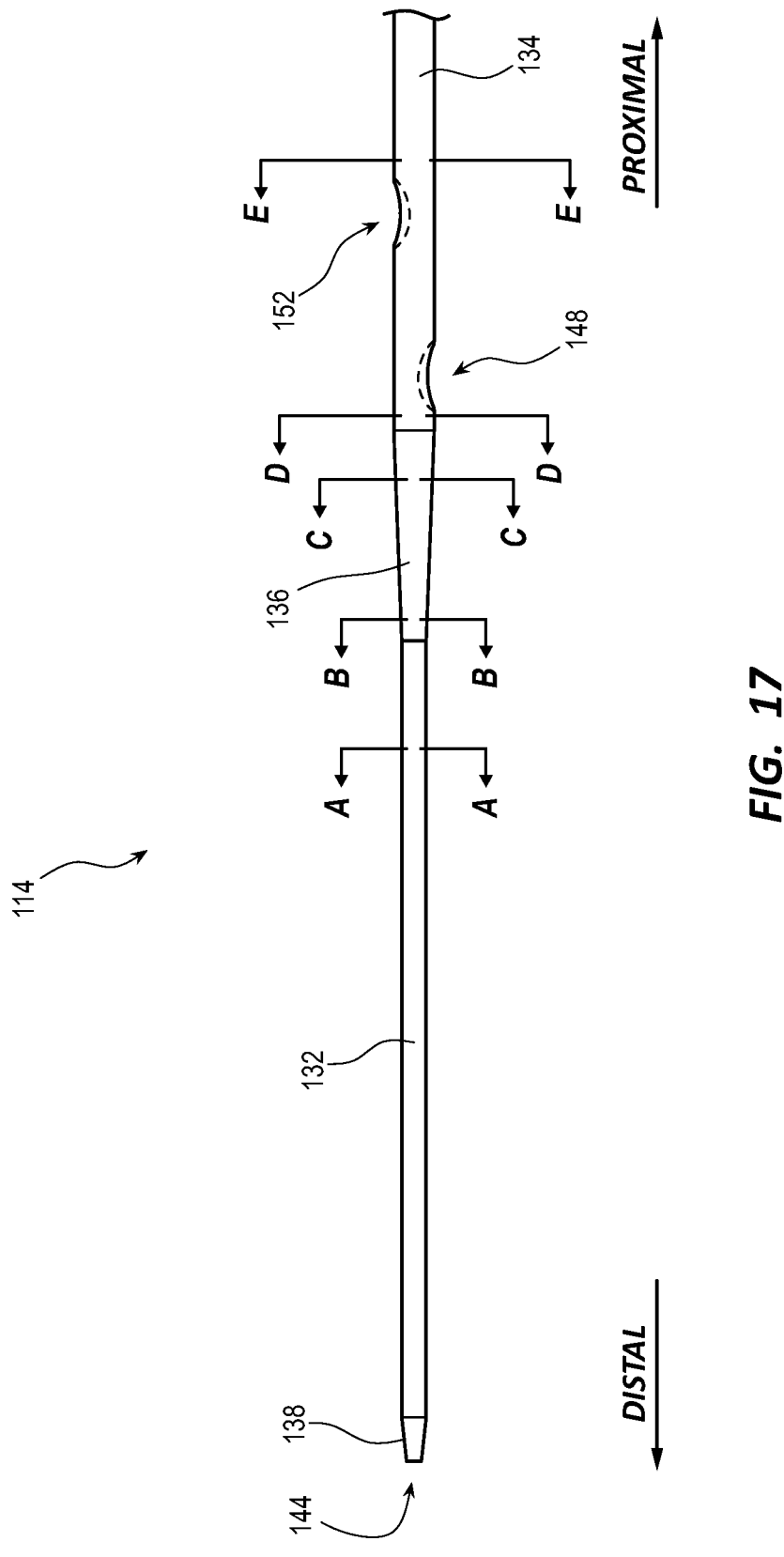
FIG. 17 illustrates a distal portion of a catheter tube of the RICC of FIGS. 13 and 14 in accordance with some embodiments.
Figure 18:
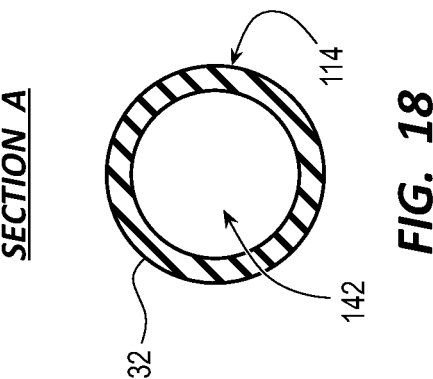
FIG. 18 illustrates a first transverse cross section of the catheter tube of FIG. 17 in accordance with some embodiments.
Figure 19:
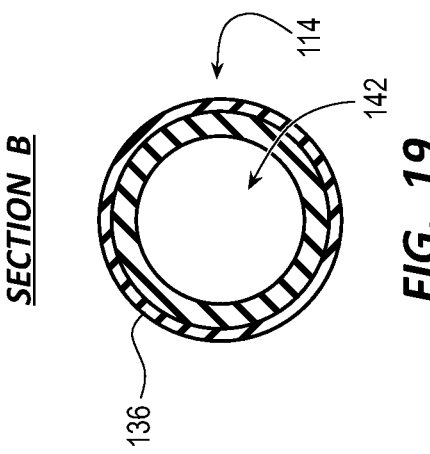
FIG. 19 illustrates a second transverse cross section of the catheter tube of FIG. 17 in accordance with some embodiments.
Figure 20:
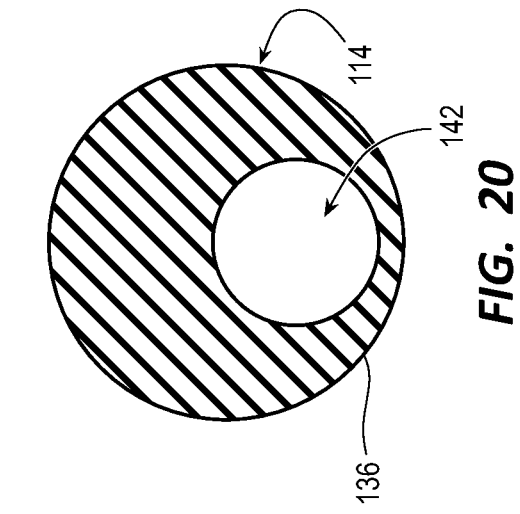
FIG. 20 illustrates a third transverse cross section of the catheter tube of FIG. 17 in accordance with some embodiments.
Figure 21:
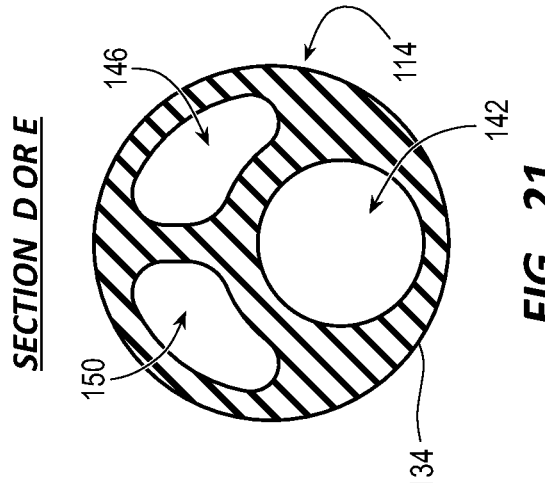
FIG. 21 illustrates a fourth or fifth transverse cross section of the catheter tube of FIG. 17 in accordance with some embodiments.

FIG. 17 illustrates a distal portion of the catheter tube 114 of the RICC 100 in accordance with some embodiments. FIGS. 18-21 illustrate various transverse cross sections of the catheter tube 114 in accordance with some embodiments.

The catheter tube 114 is coupled to the distal catheter-hub piece 112 by a proximal portion of the catheter tube 114. As such, the one-or-more distal catheter-hub lumens 120 respectively continue as one or more catheter-tube lumens. (For the one-or-more catheter-tube lumens, see the primary, secondary, and tertiary lumens 142, 146, and 150 of the RICC 100 in FIG. 21.)

The catheter tube 114 can include a hard portion and a soft portion, wherein "hard" and "soft" are used in a relative sense in that the hard portion of the catheter tube 114 is harder than the soft portion of the catheter tube 114. The hard potion of the catheter tube 114 includes a first section 132 in a distal portion of the catheter tube 114, whereas the soft potion of the catheter tube 114 includes a second section 134 extending from the proximal portion of the catheter tube 114 to the distal portion thereof but proximal of the first section 132. Notwithstanding a tapered junction 136 of the catheter tube 114 including a proximal portion of the hard portion of the catheter tube 114 disposed therein, the soft portion of the catheter tube 114 is generally considered to include the junction 136 in view of its construction. Together, the foregoing arrangement of the first section 132 of the catheter tube 114, the second section 134 of the catheter tube 114, and the junction 136 provides the catheter tube 114 with both a column strength sufficient to prevent buckling of the catheter tube 114 when inserted into an insertion site established by a percutaneous puncture and a compliance sufficient to advance the catheter tube 114 over a maneuver guidewire through a vasculature of a patient to a target location (e.g., the superior vena cava ["SVC"]).

The first section 132 of the catheter tube 114 is in the distal portion of the catheter tube 114. The first section 132 includes a distal tip 138 having a relatively short taper configured to continue from a needle tip 140 of the introducer needle 164 to an outer diameter of a remainder of the first section 132 when the introducer needle 164 is disposed in the catheter tube 114 of the distal catheter piece 104. (See FIGS. 1-4.) The short taper of the distal tip 138 is configured for immediate dilation of tissue about a percutaneous puncture established with the introducer needle 164 up to the outer diameter of the remainder of the first section 132 of the catheter tube 114. The first section 132 also includes a proximal portion disposed in the receptacle of the junction 136 set forth below and fixedly coupled (e.g., solvent bonded, adhered, welded, etc.) thereto.

The first section 132 of the catheter tube 114 is formed of a first polymeric material having a first durometer. The first polymeric material can be polytetrafluoroethylene, polypropylene, or polyurethane, but the first polymeric material is not limited to the foregoing polymers. Polyurethane is advantageous in that the first section 132 of the catheter tube 114 can be relatively rigid at room-temperature but become more flexible in vivo at body temperature, which reduces irritation to vessel walls and phlebitis.

The second section 134 of the catheter tube 114 extends from the proximal portion of the catheter tube 114 to the distal portion thereof but proximal of the first section 132 of the catheter tube 114. The second section 134 includes a distal end coupled to the junction 136 and a proximal portion disposed in the distal catheter-hub piece 112 and fixedly coupled (e.g., solvent bonded, welded, adhered, etc.) thereto.

The second section 134 of the catheter tube 114 is formed of a second polymeric material having a second durometer less than the first durometer. The second polymeric material can be polyvinyl chloride, polyethylene, polyurethane, or silicone, but the second polymeric material is not limited to the foregoing polymers. In addition to that set forth above for polyurethane in the first section 132 of the catheter tube 114, polyurethane is advantageous in that it can be less thrombogenic than some other polymers.

The junction 136 of the catheter tube 114 couples the first and second sections 132 and 134 and of the catheter tube 114 together. The junction 136 includes a receptacle in a distal portion including the proximal portion of the first section 132 of the catheter tube 114 disposed therein and fixedly coupled (e.g., solvent bonded, welded, adhered, etc.) thereto. (For the receptacle of the junction 136, see FIGS. 17 and 19, from which the receptacle can be discerned.) The junction 136 also includes a flat-faced proximal end fixedly coupled (e.g., molded together with the second section 134, solvent bonded, welded, adhered, etc.) to a flat-faced distal end of the second section 134 of the catheter tube 114, which, as coupled, effectively terminates lumens of the second section 134 of the catheter tube 114 other than that corresponding to the primary lumen 142 of the RICC 100 from passing through the junction 136. The junction 136 also includes a taper over its length from a distal end to the proximal end configured for immediate dilation of tissue about a percutaneous puncture up to an outer diameter of the second section 134 of the catheter tube 114. An abluminal surface of the junction 136 smoothly transitions from an abluminal surface of the proximal portion of the first section 132 without an edge that catches on skin when inserted into an insertion site of a patient. In addition to the edge being minimal to negligible, the edge can include solvent-inter-diffused polymeric material of the first polymeric material and the polymeric material of the junction 136, which smoothens the transition from the first section 132 of the catheter tube 114 to the junction 136.

The junction 136 of the catheter tube 114 is formed of the second polymeric material or a third polymeric material having a third durometer closer to the second durometer than the first durometer. Again, the second polymeric material can be polyvinyl chloride, polyethylene, polyurethane, or silicone, but the second polymeric material is not limited to the foregoing polymers.

Again, the first section 132 of the catheter tube 114 is formed of a first polymeric material having a first durometer, the second section 134 of the catheter tube 114 is formed of a second polymeric material having a second durometer less than the first durometer, and the junction 136 of the catheter tube 114 is formed of the second polymeric material or a third polymeric material having a third durometer closer to the second durometer than the first durometer. Being that each durometer of the second durometer and the third durometer is less than the first durometer, the soft portion of the catheter tube 114 including the second portion of the catheter tube 114 and the junction 136 is softer than the hard portion of the catheter tube 114 including the first portion of the catheter tube 114. In other words, the first durometer is greater than each durometer of the second durometer and the third durometer. Being that the first durometer is greater than each durometer of the second durometer and the third durometer, the hard portion of the catheter tube 114 including the first portion of the catheter tube 114 is harder than the soft portion of the catheter tube 114 including the second portion of the catheter tube 114 and the junction 136.

It should be understood the first durometer of the first polymeric material, the second durometer of the second polymeric material, and the third durometer of the third polymeric material can be on different scales (e.g., Type A or Type D), so the second durometer or the third durometer might not be numerically less than the first durometer. In other words, the first durometer material might not be numerically greater than the second durometer or the third durometer in view of the different scales. That said, the hardness of the second or third polymeric material can still be less than the hardness of the first polymeric material or the hardness of the first polymeric material can still be greater than the hardness of the second or third polymeric material because the different scales—each of which ranges from 0 to 100—are designed for characterizing different materials in groups of the materials having a like hardness.

Notwithstanding the foregoing, the first section 132 of the catheter tube 114, the second section 134 of the catheter tube 114, and the junction 136 can be formed of a same polymeric material or different polymeric materials having substantially equal durometers provided the column strength of the catheter tube 114 is sufficient to prevent buckling of the catheter tube 114 when inserted into an insertion site established by a percutaneous puncture and the compliance of the catheter tube 114 is sufficient to advance the catheter tube 114 through a vasculature of a patient to a target location.

Each extension leg of the one-or-more extension legs 110 is coupled to the proximal catheter-hub piece 106 by a distal portion of the extension leg. The one-or-more extension legs 110 respectively include one or more extension-leg lumens. As such, the one-or-more proximal catheter-hub lumens 118 respectively continue as the one-or-more extension-leg lumens.

Each extension leg of the one-or-more extension legs 110 typically includes a Luer connector coupled to the extension leg, through which Luer connector the extension leg and the extension-leg lumen thereof can be connected to another medical device.

Whether the RICC 100 is monoluminal with one lumen or multiluminal with a set of multiple lumens, the RICC 100 includes at least a primary lumen 142 (e.g., a distal lumen) in the connected state of the RICC 100, in which connected state the one-or-more catheter-tube lumens in the distal catheter piece 104 are respectively fluidly connected to the one-or-more extension leg lumens in the proximal catheter piece 102 across the two-piece catheter hub 108. The primary lumen 142 typically extends from a proximal end of the RICC 100 to a distal end of the RICC 100 such as from an opening of a corresponding Luer connector to a primary-lumen aperture 144 (e.g., a distal-lumen aperture) in a distal end of the RICC 100. When the RICC 100 has two or more lumens, the RICC 100 further includes at least a secondary lumen 146 (e.g., a medial lumen). The secondary lumen 146 typically extends from the proximal end of the RICC 100 to a distal portion of the RICC 100 such as from an opening of a corresponding Luer connector to a secondary-lumen aperture 148 (e.g., a medial-lumen aperture) in the distal portion of the catheter tube 114 proximal of the primary-lumen aperture 144. When the RICC 100 has three or more lumens, the RICC 100 further includes at least a tertiary lumen 150 (e.g., a proximal aperture). The tertiary lumen 150 typically extends from the proximal end of the RICC 100 to the distal portion of the RICC 100 such as from an opening of a corresponding Luer connector to a tertiary-lumen aperture 152 (e.g., a proximal-lumen aperture) in the distal portion of the catheter tube 114 proximal of the secondary-lumen aperture 148. Notwithstanding the foregoing, each lumen of the secondary lumen 146 and the tertiary lumen 150 can distally extend slightly farther than the secondary-lumen aperture 148 and the tertiary-lumen aperture 152, respectively, in view of different manufacturing methods. As set forth above, however, the flat-faced proximal end of the junction 136 is fixedly coupled (e.g., molded together with the second section 134, solvent bonded, welded, adhered, etc.) to the flat-faced distal end of the second section 134 of the catheter tube 114, which, as coupled, effectively terminates lumens such as the secondary and tertiary lumen 150s and from passing through the junction 136.

Introducers and Introducer Assemblies

FIGS. 1-4 illustrate various view of an introducer assembly 154 including an introducer 156 and the distal catheter piece 104 of the two-piece RICC 100 in accordance with some embodiments.

As shown, the introducer 156 is configured to couple to the distal catheter piece 104 of the two-piece RICC 100 to form the introducer assembly 154. Indeed, FIGS. 1-4 show the introducer 156 coupled with the distal catheter piece 104 in a ready-to-deploy state of the introducer assembly 154 (e.g., ready for a venipuncture). The introducer assembly 154 is configured to be actuated in at least three ways with a single finger (e.g., index finger) of a hand while the introducer assembly 154 is held between a thumb and another finger or fingers (e.g., middle and ring fingers) of the same hand. Thus, a number of operating states of the introducer assembly 154 are also possible, some of which operating states are either identified in or discernable from the description set forth below including that of the methods for at least using the RICC systems provided herein.

The introducer 156 includes a catheter-advancement hub 158, an introducer housing 160, and a syringe 162 including an introducer needle 164. Description for the catheter-advancement hub 158, the introducer housing 160, and the

15

16 syringe 162 is presented, in turn, below followed by some other features of the introducer 156; however, some crossover between the description for the catheter-advancement hub 158, the introducer housing 160, the syringe 162, and the other features of the introducer 156 exists in view of the interrelatedness of the foregoing features in the introducer 156. Again, some of the description for the introducer 156 is also presented in the context of introducer assemblies in view of the interrelatedness of the introducer 156 and the RICCs.

Figure 12:
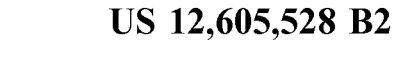
FIG. 12 illustrates a catheter-advancement hub coupled to a distal catheter-hub piece of the distal catheter piece in the ready-to-deploy state of the introducer assembly in accordance with some embodiments.

FIG. 12 illustrates the catheter-advancement hub 158 coupled to the distal catheter-hub piece 112 of the distal catheter piece 104 in the ready-to-deploy state of the introducer assembly 154 in accordance with some embodiments.

As shown, the catheter-advancement hub 158 is configured to couple to the distal catheter piece 104 in the introducer assembly 154. Indeed, FIG. 12 shows the catheter-advancement hub 158 coupled with a proximal portion of the distal catheter-hub piece 112 in the ready-to-deploy state of the introducer assembly 154.

The catheter-advancement hub 158 includes a manifold 166, a side arm 168, and a catheter-advancement push tab 170 proximally extending from the side arm 168. As best seen in FIG. 12, the catheter-advancement hub 158 includes an integrated proximal connector (e.g., a female Luer connector) configured to fluidly couple the syringe 162 to the catheter-advancement hub 158 by way of the syringe tip. Such a fluid coupling between the catheter-advancement hub 158 and the syringe 162 is useful for observing blood flashback in the hub 204 of the syringe 162, if present, upon establishing a needle tract to a blood-vessel lumen of a patient.

The manifold 166 includes one or more manifold lumens 172 equal in number to the one-or-more distal catheter-hub lumens 120, which catheter-hub lumens respectively continue as the one-or-more catheter-tube lumens in the distal catheter piece 104 as set forth above. In the ready-to-deploy state of the introducer assembly 154, the one-or-more manifold lumens 172 are fluidly connected to the one-or-more catheter-tube lumens by way of the one-or-more distal catheter-hub lumens 120 such that the one-or-more catheter-tube lumens can be simultaneously primed with a fluid (e.g., saline, heparinized saline, etc.) before inserting the distal catheter piece 104 or the catheter tube 114 thereof into a blood-vessel lumen of a patient.

As best seen in FIG. 12, the side arm 168 of the catheter-advancement hub 158 includes an integrated side-arm connector (e.g., a female Luer connector) and a side-arm lumen 174 fluidly coupled to the one-or-more manifold lumens 172. A combination of the side-arm lumen 174 and the one-or-more manifold lumens 172 is thusly configured for the simultaneous priming of each lumen of the one-or-more catheter-tube lumens before inserting the distal catheter piece 104 or the catheter tube 114 into the blood-vessel lumen of the patient. A needle shaft of the introducer needle 164 extends through the manifold 166, or at least one manifold lumen thereof, and a distal end of the distal catheter piece 104 in the ready-to-deploy state of the introducer assembly 154. As such, the simultaneous priming of each lumen of the one-or-more catheter-tube lumens occurs around the introducer needle 164 in the at-least-one manifold lumen when the simultaneous priming is performed.

The catheter-advancement push tab 170 is configured for distally advancing the catheter-advancement hub 158 and, thus, the distal catheter piece 104 via the distal catheter-hub piece 112 coupled thereto by pushing the catheter-advancement push tab 170 with a single finger (e.g., index finger) of a hand while holding the syringe 162 around a distal portion thereof between the thumb and another finger or fingers (e.g., middle and ring fingers) of the same hand. Again, the catheter-advancement push tab 170 proximally extends from the side arm 168 of the catheter-advancement hub 158. Indeed, in the ready-to-deploy state of the introducer assembly 154, the catheter-advancement push tab 170 proximally extends over a portion of the plunger-withdrawal push tab 212 set forth below, which, in turn, proximally extends over the distal portion of the syringe 162. The foregoing arrangement of the plunger-withdrawal push tab 212 and the catheter-advancement push tab 170 makes the push tabs 170 and 212 immediately accessible for actuating the introducer assembly 154 with the single finger while holding the syringe 162 around the distal portion thereof between the thumb and the other finger or fingers of the same hand as the single finger.

Figure 6:
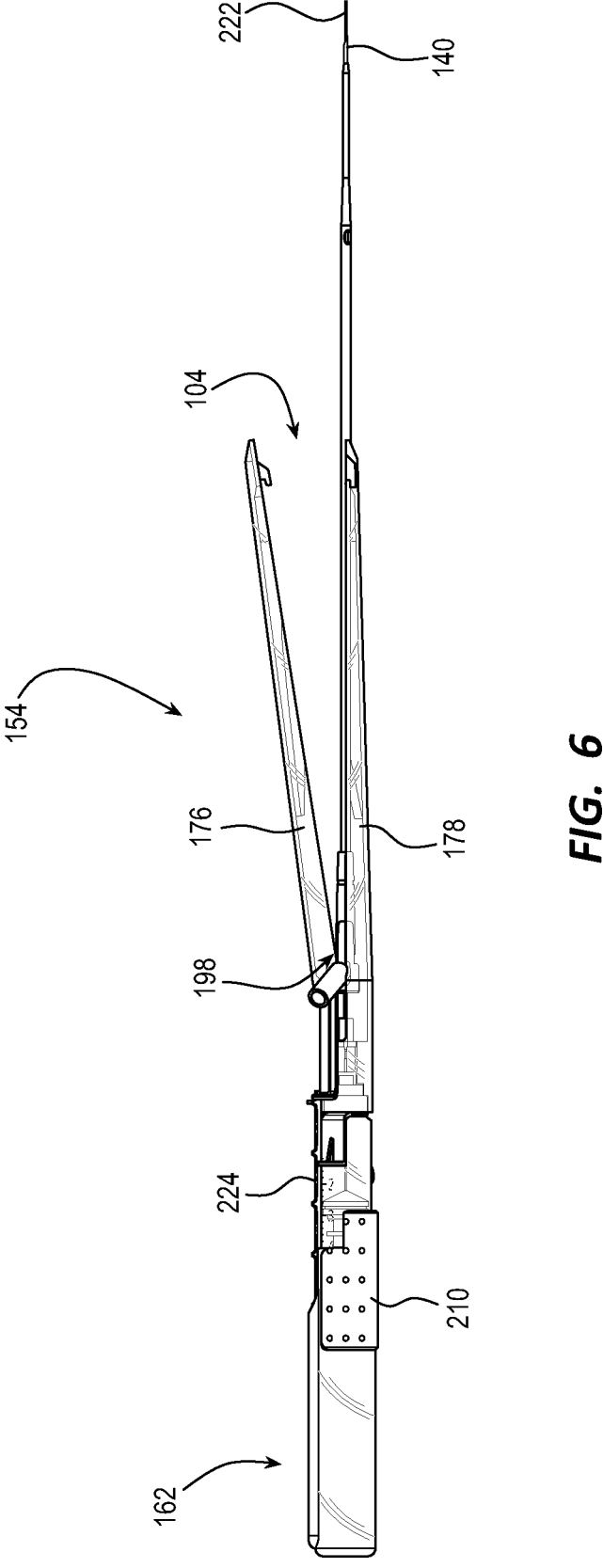
FIG. 6 illustrates a side view of the introducer assembly in another operating state with a split introducer housing and the distal catheter piece of the RICC advanced from a ready-to-deploy state of the introducer assembly in accordance with some embodiments.
Figure 7:
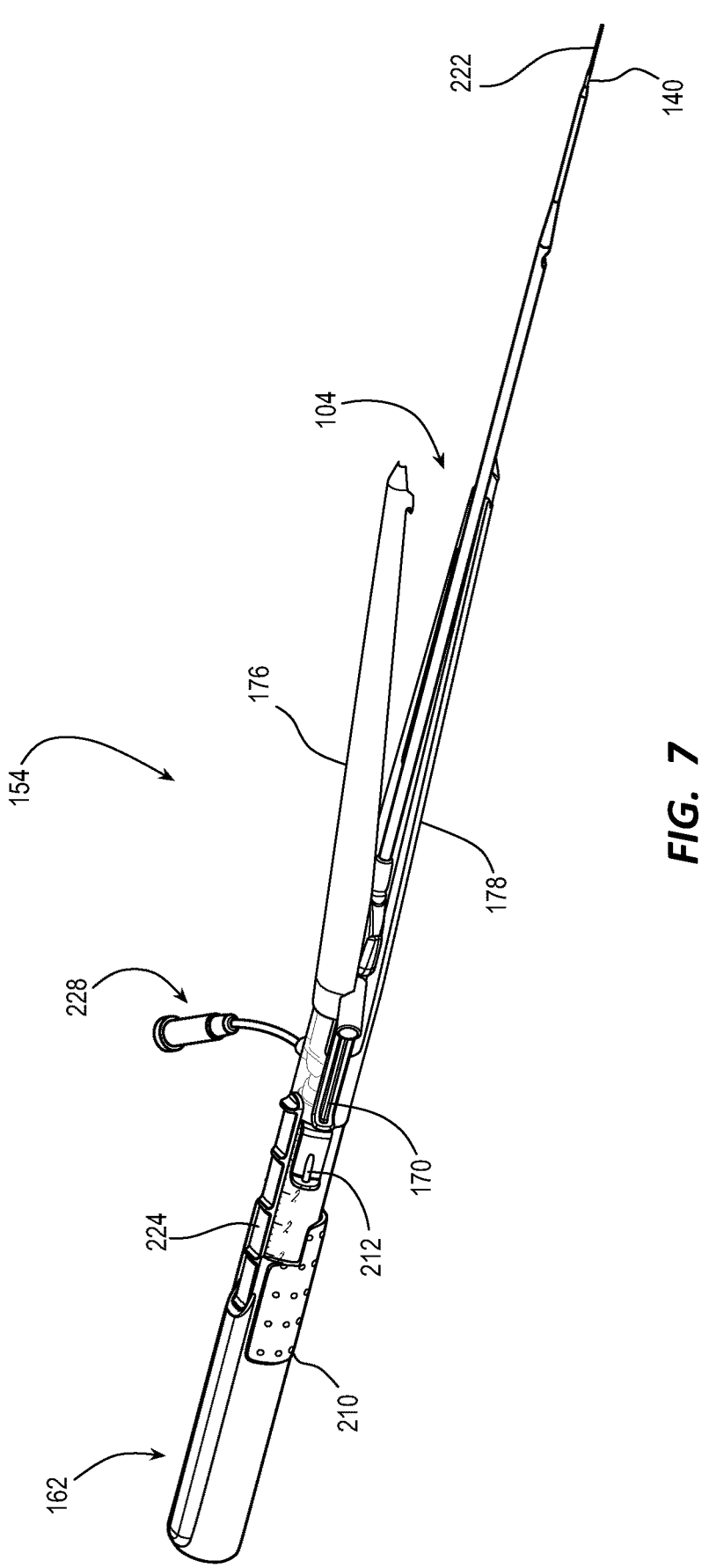
FIG. 7 illustrates an oblique view of the introducer assembly in the same operating state as FIG. 6 in accordance with some embodiments.

FIGS. 6 and 7 illustrate different views of the introducer assembly 154 in an operating state with the introducer housing 160 split along its length in accordance with some embodiments.

As shown, the introducer housing 160 includes two pieces including a slidable piece 176 and a stationary piece 178 configured to split open along a length of the introducer housing 160. Indeed, in the ready-to-deploy state of the introducer assembly 154 shown in FIGS. 1-4, the introducer housing 160 is closed over the syringe tip to which the stationary piece 178 is coupled, the manifold 166, and a proximal portion of the distal catheter piece 104, whereas the introducer housing 160 is split open in the operating state of the introducer assembly 154 shown in FIGS. 6 and 7. The introducer housing 160 is configured to provide column strength to the catheter tube 114 of the distal catheter piece 104 for a venipuncture (e.g., the needle tract-establishing step set forth below) with the introducer needle 164 while the introducer assembly 154 is in the ready-to-deploy state. In addition, at least a proximal portion of the catheter tube 114 is ensconced in the introducer housing 160 in the ready-to-deploy state of the introducer assembly 154, thereby providing a no-touch mechanism for not touching and contaminating the catheter tube 114 during the venipuncture.

Figure 9:
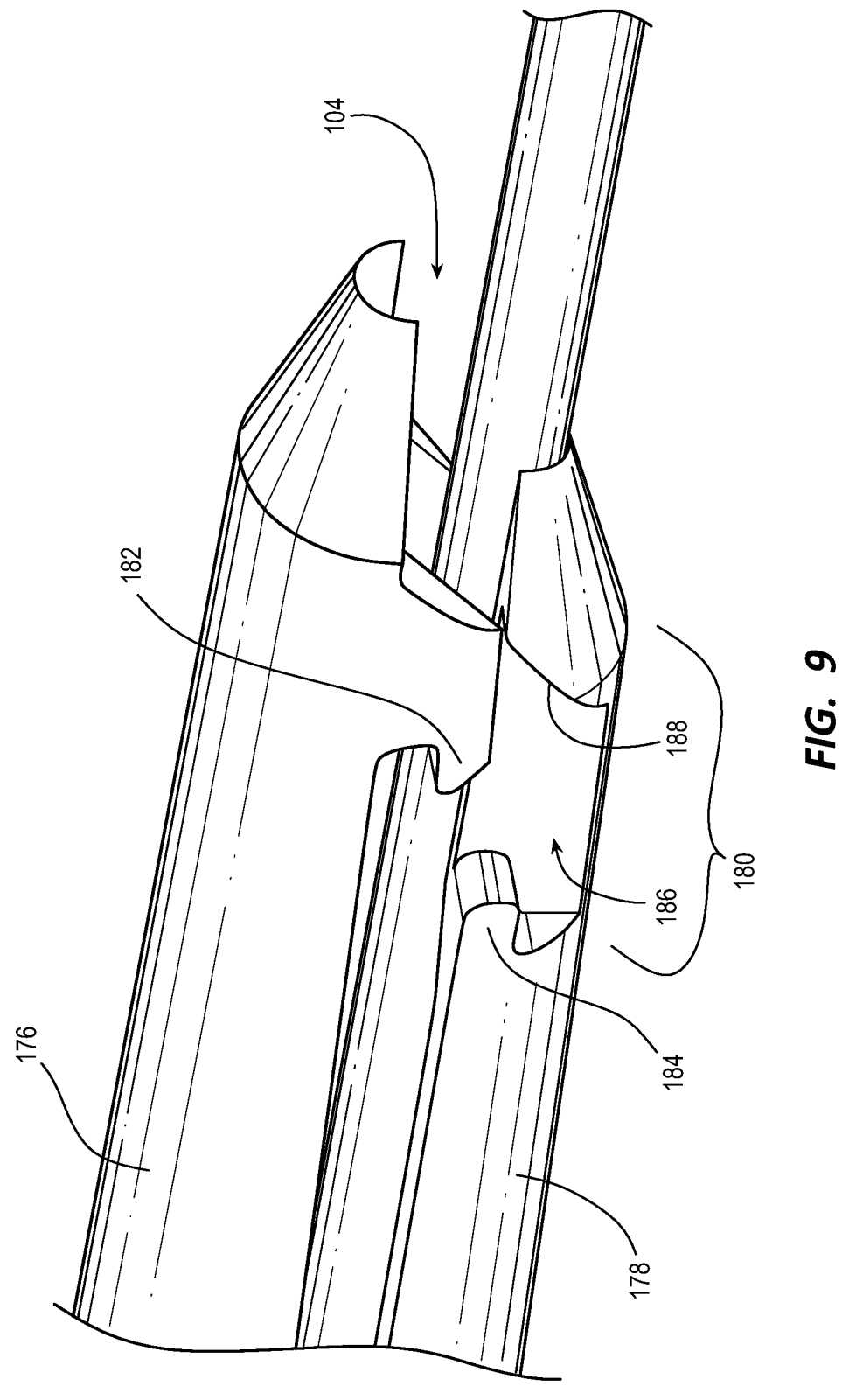
FIG. 9 illustrates a lock in a distal portion of the introducer housing in accordance with some embodiments.

FIG. 9 illustrates a lock 180 in a distal portion of the introducer housing 160 in accordance with some embodiments.

As shown, the lock 180 includes a hook 182 in the slidable piece 176 of the introducer housing 160 and a latch 184 in the stationary piece 178 of the introducer housing 160. Each of the hook 182 and the latch 184 can be integral (e.g., molded) with its respective piece of the introducing housing; that is, the hook 182 can be integral with the slidable piece 176 and the latch 184 can be integral with the stationary piece 178. The hook 182 and latch 184 are configured to lock the slidable piece 176 and the stationary piece 178 together in the ready-to-deploy state of the introducer assembly 154.

The stationary piece 178 of the introducer housing 160 also includes a channel 186, which can be molded into the stationary piece 178. The channel 186, in turn, includes the latch 184 in a proximal portion of the channel 186 and a ramp 188 in a distal portion of the channel 186. As with the latch 184, the ramp 188 can be integral (e.g., molded) with the stationary piece 178. A combination of the ramp 188 and the hook 182 of the slidable piece 176 of the introducer housing 160 are configured to push the slidable piece 176 away from the stationary piece 178 while distally advancing the slidable piece 176 relative to the stationary piece 178. Indeed, a distal face of the hook 182 engages a proximal face of the ramp 188 while distally advancing the slidable piece 176 relative to the stationary piece 178, which lifts the hook 182 out of the channel 186 and pushes the slidable piece 176 away from the stationary piece 178, thereby longitudinally splitting the introducer housing 160 open.

Figure 8:
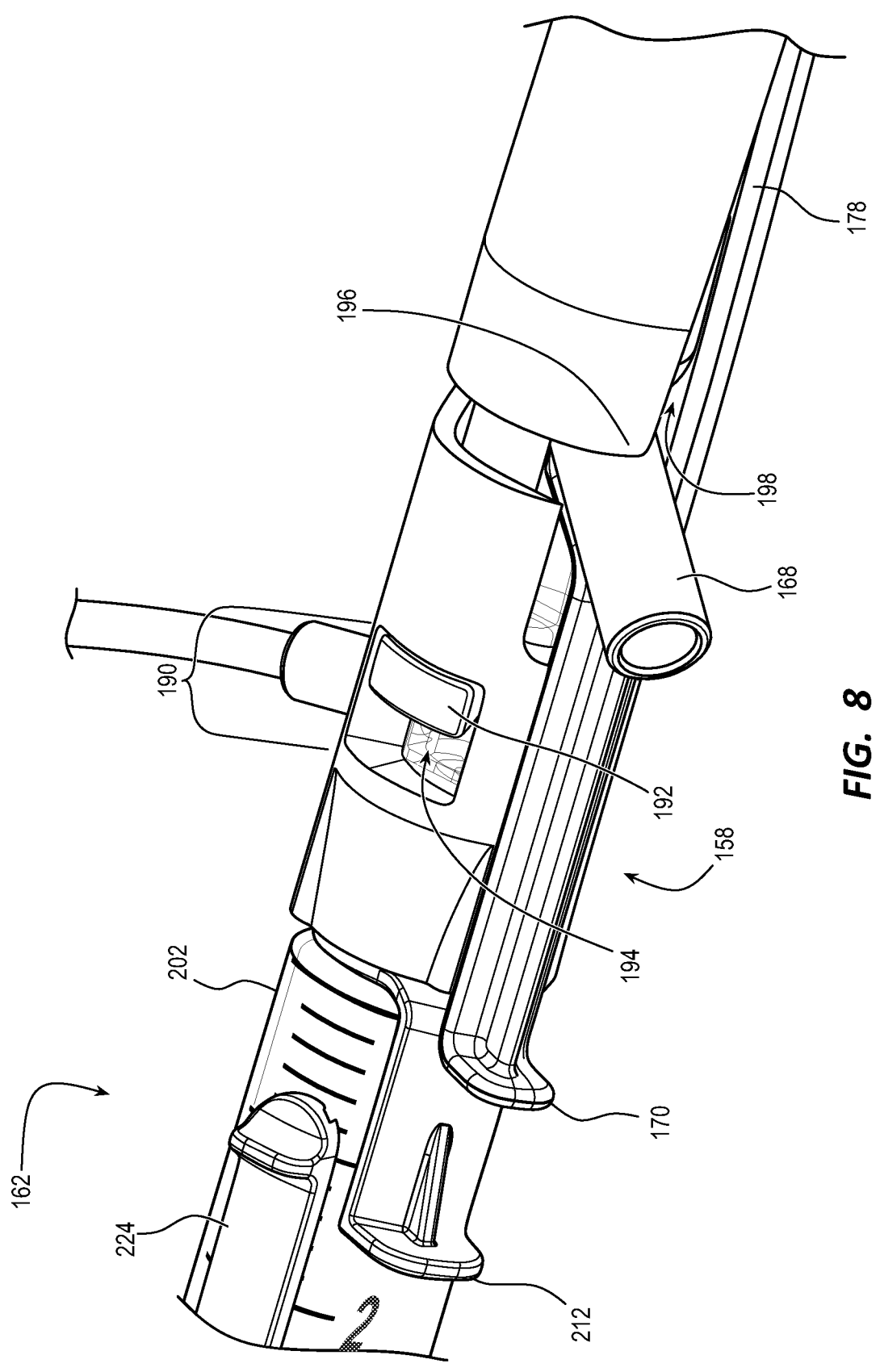
FIG. 8 illustrates a sliding hinge in a proximal portion of the introducer housing in accordance with some embodiments.

FIG. 8 illustrates a sliding hinge 190 in a proximal portion of the introducer housing 160 in accordance with some embodiments.

As shown, the sliding hinge 190 includes a captive tab 192 of the slidable piece 176 of the introducer housing 160 and a track 194 in the stationary piece 178 of the introducer housing 160. As with the hook 182, the captive tab 192 can be integral (e.g., molded) with the slidable piece 176. Like the channel 186, the track 194 can be molded into the stationary piece 178. The captive tab 192 is captively but slidably disposed in the track 194 allowing the slidable piece 176 to be distally advanced relative to the stationary piece 178 without separating the slidable piece 176 from the stationary piece 178 in the proximal portion of the introducer housing 160. That said, distally advancing the slidable piece 176 relative stationary piece 178 separates the slidable piece 176 from the stationary piece 178 in the distal portion of the introducer housing 160 as set forth above. Indeed, a proximal portion of the captive tab 192 inboard of an exterior surface of the introducer housing 160 is undercut or radiused, which facilitates smoothly splitting the slidable piece 176 from the stationary piece 178 in the distal portion of the introducer housing 160 while distally advancing the slidable piece 176 relative to the stationary piece 178.

As further shown in FIG. 8, the proximal portion of the introducer housing 160 includes an introducer-housing tab 196 and a longitudinal cutout 198 that narrows as the introducer housing 160 tapers from the proximal portion to the distal portion of the introducer housing 160.

The introducer-housing tab 196 is configured to provide a point of the introducer housing 160 against which the side arm 168 of the catheter-advancement hub 158 can push while the catheter-advancement hub 158 is distally advanced within the introducer housing 160. Indeed, the foregoing arrangement of the introducer-housing tab 196 and the side arm 168 of the catheter-advancement hub 158 makes it such that the slidable piece 176 of the introducer housing 160 can be distally advanced relative to the stationary piece 178 of the introducer housing 160 by pushing the catheter-advancement push tab 170 as set forth above.

The longitudinal cutout 198 is configured to provide a narrowing path for the side arm 168 of the catheter-advancement hub 158 to follow while distally advancing the catheter-advancement hub 158, which narrowing path, in turn, is configured for side arm-based separation of the slidable piece 176 from the stationary piece 178 while distally advancing the side arm 168 of the catheter-advancement hub 158 through the narrowing path. For example, when the hook 182 of the slidable piece 176 is lifted out of the channel 186 by the ramp 188 of the stationary piece 178 while distally advancing the slidable piece 176 relative to the stationary piece 178 by the catheter-advancement hub 158, the introducer-housing tab 196 pivots over the side arm 168 allowing the side arm 168 to enter the narrowing path provided by the longitudinal cutout 198. Because the longitudinal cutout 198 narrows from the proximal portion to the distal portion of the introducer housing 160, the side arm 168 of the catheter-advancement hub 158 continues to lift and separate the slidable piece 176 from the stationary piece 178 until the side arm 168 exits the longitudinal cutout 198. Once the introducer housing 160 is sufficiently split open and the distal catheter piece 104 of the RICC 100 distally advanced from its initial position in the ready-to-deploy state of the introducer assembly 154, the distal catheter-hub piece 112 is available for manually decoupling the distal catheter-hub piece 112 from the manifold 166 of the catheter-advancement hub 158 and removing the distal catheter piece 104 from the introducer housing 160.

Notably, the introducer housing 160 is configured such that the slidable piece 176 and the stationary piece 178 remain locked together by the lock 180 thereof until after a venipuncture when the catheter-advancement hub 158 is advanced as set forth above.

Figure 10:
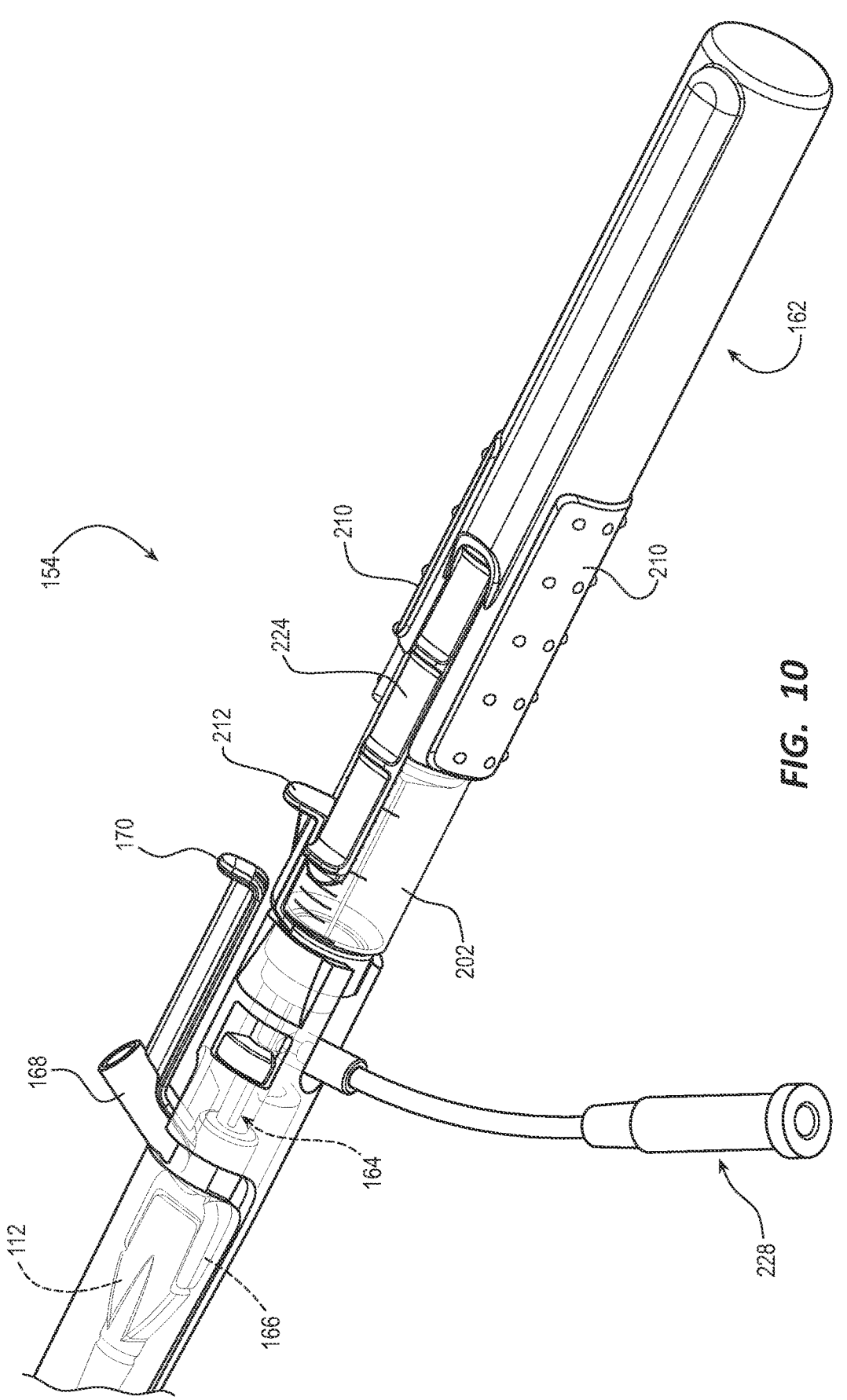
FIG. 10 illustrates a syringe of the introducer in accordance with some embodiments.

FIG. 10 illustrates the syringe 162 of the introducer 156 in accordance with some embodiments.

The syringe 162 includes a plunger 200 disposed in a barrel 202 having a distal portion terminating in a syringe tip to which the introducer needle 164 is fluidly coupled and fixedly attached. As best seen in FIG. 12, the syringe tip includes a syringe-tip connector (e.g., a male Luer connector), which is configured to be fluidly coupled to the catheter-advancement hub 158 by way of the proximal coupler thereof in at least the ready-to deploy state of the introducer assembly 154. Optionally, the syringe tip can include a hub 204 and a side arm 206 coupled to the fluid-pressure indicator 228 set forth below. In addition, the syringe 162 includes a syringe housing 208 around the barrel 202. As set forth below, the syringe housing 208 is configured for holding the syringe 162 around the distal portion of the barrel 202 between the thumb and another finger or fingers (e.g., middle or ring fingers) of a hand while reserving a single finger (e.g., index finger) of the same hand for actuating the introducer assembly 154. Holding and handling the introducer assembly 154 in accordance with the foregoing provides better control of the introducer assembly 154 and the distal catheter piece 104 thereof, particularly during a venipuncture.

The syringe housing 208 extends from a distal end in a distal portion of the syringe housing 208 around the distal portion of the barrel 202 of the syringe 162 to a proximal end in a proximal portion of the syringe housing 208 approximately coextensive with a proximal portion of the barrel 202. The syringe housing 208 can include a gripping portion 210 (e.g., a pattern of bumps, through holes, etc.) in the distal portion thereof configured to facilitate gripping the syringe 162 and, thus, the introducer 156 or introducer assembly 154 of which it is part around the distal portion of the barrel 202 between the thumb and the other finger or fingers of the same hand as set forth above. Distal placement of the gripping portion 210 about the distal portion of the barrel 202 encourages holding and handling the introducer assembly 154 in a location that provides better control of a distal portion of the introducer assembly 154, for example, the first section 132 of the catheter tube 114 of the distal catheter piece 104. Indeed, by holding and handling the introducer assembly 154 in the foregoing location, small inadvertent yaw- or pitch-type movements there remain relatively small in the first section 132 of the catheter tube 114 compared to the same type of movements when the introducer assembly 154 is held in a more proximal location.

The syringe housing 208 and the plunger 200 are configured to operate together as a single unit insofar as actuating the syringe 162 (e.g., withdrawing the plunger 200 for the blood-aspirating step set forth below). The syringe housing 208 and the plunger 200 or the end piece 220 thereof can be molded together in an integral piece such that the proximal portion of the syringe housing 208 is integral with a proximal portion of the plunger 200. Alternatively, the syringe housing 208 and the plunger 200 or the end piece 220 thereof can be separately molded and subsequently coupled together in a coupled piece such that the proximal portion of the syringe housing 208 is coupled to the proximal portion of the plunger 200 or the end piece 220 thereof. For example, an inner wall in a proximal end of the syringe housing 208 can be bonded or welded to a plunger flange of a distal end of the plunger 200 or the end piece 220 thereof. Whether the syringe housing 208 and the plunger 200 are integral with or coupled to each other, proximally sliding the syringe housing 208 relative to the barrel 202 withdraws the plunger 200 from the barrel 202, thereby actuating the syringe 162 as a single unit.

The syringe 162 can further include a plunger-withdrawal push tab 212 proximally extending over the barrel 202 from the distal portion of the barrel 202 (e.g., the syringe tip) to which the plunger-withdrawal push tab 212 is coupled, for example, by a ring-type coupler. (See FIG. 12.) The plunger-withdrawal push tab 212 is configured for use when actuating the syringe 162 as set forth above. Indeed, the plunger-withdrawal push tab 212 is configured for pushing against with a single finger (e.g., index finger) of a hand while holding the syringe housing 208 around the distal portion of the barrel 202 between the thumb and another finger or fingers (e.g., middle and ring fingers) of the same hand, which proximally slides the syringe housing 208 relative to the barrel 202 and withdraws the plunger 200 from the barrel 202.

Figure 11:
FIG. 11 illustrates a longitudinal cross section of a portion of the syringe in accordance with some embodiments.

FIG. 11 illustrates a longitudinal cross section of a portion of the syringe 162 in accordance with some embodiments.

As shown, the syringe 162 also includes a syringe portion of an access-guidewire lumen 214 formed of fluidly connected portions of a plunger lumen of the plunger 200, a syringe-tip lumen of the syringe tip, and any space within the barrel 202 formed by pulling the plunger 200 partially out of the barrel 202 such as in an operating state of the introducer assembly 154 (e.g., during the blood-aspirating step of the method set forth below). Another portion of the access-guidewire lumen 214 is the introducer-needle portion of the access-guidewire lumen 214, namely a needle lumen of the introducer needle 164.

The plunger 200 includes a sealing mechanism 216 in a distal portion of the plunger 200 for sealing off the access-guidewire lumen 214 distal of the sealing mechanism 216. The sealing mechanism 216 is configured to seal off the access-guidewire lumen 214 to maintain a vacuum for aspirating blood when the plunger 200 is withdrawn from the barrel 202. The sealing mechanism 216 is also configured to seal off the access-guidewire lumen 214 to prevent blood from discharging (e.g., flashing back) through the longitudinal slots of the barrel 202 and the plunger 200 set forth below during a venipuncture or while withdrawing the access guidewire 222 set forth below from a blood-vessel lumen of a patient, thereby minimizing or preventing a potential for contaminating an operating field or any clinicians within the operating field.

As shown in FIG. 11, the sealing mechanism 216 can be a cartridge disposed in a cavity in a distal portion of a main body 218 of the plunger 200 and held in the cavity by an end piece 220 of the plunger 200. The cartridge is coaxially aligned with the access-guidewire lumen 214 or the plunger-lumen portion thereof such that an unwrapped, bare-wire portion an access guidewire 222 passes through proximal- and distal-end through holes of the cartridge, which have inner diameters commensurate with an outer diameter of the bare-wire portion of the access guidewire 222. Optionally, the sealing mechanism 216 includes one or more gaskets such as 'O'-rings within the cartridge or as an alternative to the cartridge. Instead of the cartridge, for example, the one-or-more 'O'-rings can be axially compressed in the cavity by the end piece 220 of the plunger 200, which, in turn, radially compresses the 'O'-rings around the access guidewire 222, thereby sealing off the access-guidewire lumen 214.

Figure 5:
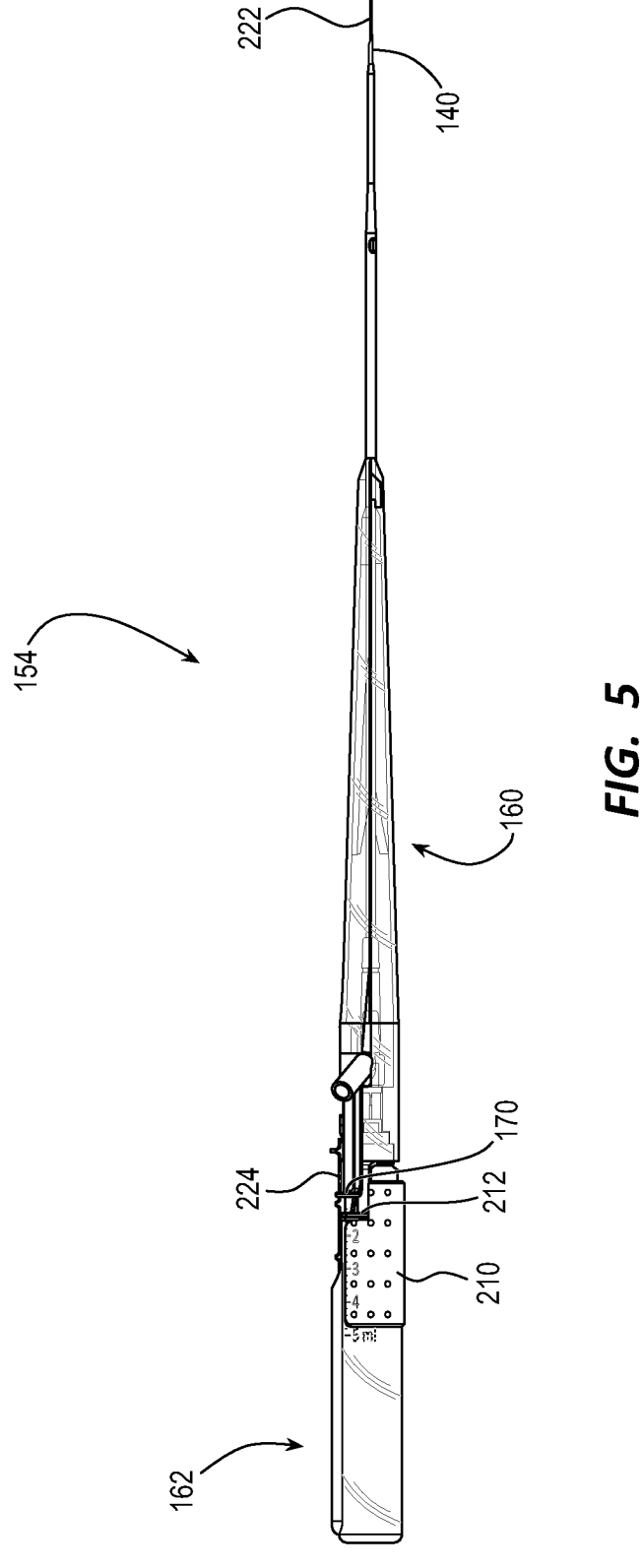
FIG. 5 illustrates a side view of the introducer assembly in an operating state with an access guidewire advanced through a distal end of the distal catheter piece of the RICC in accordance with some embodiments.

FIG. 5 illustrates a side view of the introducer assembly 154 in another operating state with the access guidewire 222 advanced through the distal end of the distal catheter piece 104 in accordance with some embodiments.

The access guidewire 222 is captively disposed in the introducer 156 such that at least a portion of the access guidewire 222 is always in a portion (e.g., the plunger-lumen portion, the needle-lumen portion, etc.) of the access-guidewire lumen 214 no matter the state of the introducer assembly 154. For example, when the access guidewire 222 is withdrawn to its proximal limit (e.g., defined by the proximal ends of the longitudinal slots set forth below), a proximal portion of the access guidewire 222 is disposed in at least a proximal portion of the plunger lumen. Meanwhile, a distal portion of the access guidewire 222 is disposed in a distal portion of the needle lumen. When the introducer assembly 154 is in at least the ready-to-deploy state thereof, the proximal portion of the access guidewire 222 is disposed in a medial portion of the plunger lumen and the distal portion of the access guidewire 222 remains disposed in the distal portion of the needle lumen; however, a distal end of the access guidewire 222 is advanced in the needle lumen such that the distal end of the access guidewire 222 is just short of the needle tip 140. And when the access guidewire 222 is advanced to its distal limit (e.g., defined by the distal ends of the longitudinal slots set forth below) in some operating states of the number of operating states of the introducer assembly 154 (e.g., during the access guidewire-advancing step of the method set forth below), the proximal portion of the access guidewire 222 is disposed in a distal portion of the plunger lumen. Meanwhile, as result of its length, the distal end of the access guidewire 222 extends through or beyond the distal end of the distal catheter piece 104, which is sufficient for extension of the access guidewire 222 into a blood vessel lumen of a patient upon establishing access thereto after the needle tract-establishing step set forth below.

The syringe 162 also includes a slider 224 (e.g., a tabbed slider) distally extending over the barrel 202 from under the syringe housing 208. The slider 224 is configured for actuating the access guidewire 222 with a single finger (e.g., an index finger) of a hand (e.g., with a scroll wheel-type motion of the finger like that used on a computer mouse) while holding the distal portion of the syringe housing 208 between the thumb and another finger or fingers (e.g., middle and ring fingers) of the same hand. The slider 224 includes an extension 226 extending through a longitudinal slot (not shown) in each of the barrel 202 and the plunger 200 into the access-guidewire lumen 214 proximal of the sealing mechanism 216 where the extension 226 is coupled to the access guidewire 222. Proximal and distal ends of the longitudinal slots provide stops for the extension 226 and, therefore, a limited tract within which the extension 226 can proximally or distally move, thereby providing proximal and distal limits for respectively withdrawing or advancing the access guidewire 222 into or from the introducer 156.

FIG. 10 illustrates the syringe 162 of the introducer 156 including a fluid-pressure indicator 228 in accordance with some embodiments.

As shown, the fluid-pressure indicator 228, when present, extends from the side arm 206 of the hub 204. The fluid-pressure indicator 228 includes a closed end and an open end fluidly coupled to the needle lumen of the introducer needle 164 by way of a side-arm lumen of the side arm. The fluid-pressure indicator 228 is configured as a built-in accidental arterial indicator, wherein blood under sufficient pressure (e.g., arterial blood) can enter the fluid-pressure indicator 228 and compress a column of air within the fluid-pressure indicator 228. However, it is also possible to observe blood flashback from a venipuncture in the fluid-pressure indicator 228 in some cases. That said, the blood flashback from the venipuncture is normally observed in the hub 204, the side arm of the hub 204, or the syringe 162.

Methods

Methods for the RICC systems provided herein include at least methods of using the RICC systems. Such a method of using a RICC system can include a RICC system-obtaining step, a needle tract-establishing step, a first RICC-advancing step, an introducer housing-splitting step, and an introducer-removing step.

The RICC system-obtaining step includes obtaining the RICC system. As set forth above, the RICC system includes the proximal catheter piece 102 of the RICC 100 and the introducer assembly 154. The introducer assembly 154, in turn, includes the distal catheter piece 104 of the RICC 100 partially disposed in the introducer housing 160 of the introducer 156.

The method can further include a needle tip-ensuring step before the needle tract-establishing step. Again, the introducer needle 164 has the needle shaft extending through the distal end of the distal catheter piece 104 in the ready-to-deploy state of the introducer assembly 154. The needle tip-ensuring step includes ensuring the needle tip 140 extends from the distal end of the distal catheter piece 104 before the needle tract-establishing step.

The method can further include a priming step before the needle tract-establishing step. The priming step includes priming the distal catheter piece 104 with a common syringe through the side arm 168 of the catheter-advancement hub 158 before the first RICC-advancing step. As set forth above, the side arm 168 has the side-arm lumen 174 fluidly coupled to the one-or-more manifold lumens 172 for simultaneously priming each lumen of the respective one or more lumens of the distal catheter piece 104.

The needle tract-establishing step includes establishing a needle tract from an area of skin to a blood-vessel lumen of a patient with the introducer needle 164 of the introducer. The needle tract-establishing step is performed while holding the distal portion of the syringe 162 of the introducer 156 between the thumb and another finger or fingers (e.g., ring and middle fingers) of a hand. Meanwhile, at least a single finger (e.g., index finger) of the same hand is kept readily available for actuating the introducer assembly 154.

The needle tract-establishing step can further include ensuring blood flashes back into the hub 204, the side arm of the hub 204, or the fluid-pressure indicator 228 extending from the side arm of the hub 204 upon establishing the needle tract.

The method further includes a blood-aspirating step. The blood-aspirating step includes aspirating blood with the syringe 162 to confirm the needle tip 140 of the introducer needle 164 is disposed in the blood-vessel lumen before the introducer-removing step. The blood-aspirating step includes pushing the plunger-withdrawal push tab 212 with the single finger of the hand while holding the distal portion of the syringe 162 by the syringe housing 208 over the barrel 202 of the syringe 162 between the thumb and the other finger or fingers of the same hand. The plunger-withdrawal push tab 212 extends over the barrel 202 from the distal portion of the syringe 162 such that pushing the plunger-withdrawal tab while holding the distal portion of the syringe 162 by the syringe housing 208 proximally slides the syringe housing 208 relative to the barrel 202 and withdraws the syringe housing-connected plunger 200 from the barrel 202.

The method can further include an access guidewire-advancing step. The access guidewire-advancing step includes advancing the access guidewire 222 disposed in the access-guidewire lumen 214 into the blood-vessel lumen beyond the distal end of the distal catheter piece 104. As set forth above, the access-guidewire lumen 214 is formed of at least the plunger lumen of the syringe 162 and the needle lumen of the introducer needle 164, and the distal end of the access guidewire 222 is in the needle lumen just short of the needle tip 140, which facilitates first-stick success by making the access guidewire 222 immediately available before the blood-lumen vessel can be lost due to small inadvertent movements. In addition, the slider 224 is coupled to the access guidewire 222 such that distally advancing the slider 224 with the single finger of the hand while holding the distal portion of the syringe housing 208 between the thumb and the other finger or fingers of the same hand advances the access guidewire 222 into the blood-vessel lumen. The access guidewire-advancing step is performed before the first RICC-advancing step.

The first RICC-advancing step includes advancing the distal portion of the first section 132 of the catheter tube 114 of the distal catheter piece 104 into the blood-vessel lumen over the needle shaft. As set forth above, the catheter tube 114 includes the first section 132 formed of the first material having the first durometer and the second section 134 formed of the second material having the second durometer less than the first durometer. The first section 132 of the catheter tube 114 is configured with a column strength for advancing the catheter tube 114 into the blood-vessel lumen over the access guidewire 222 or the maneuver guidewire after the maneuver guidewire-advancing step set forth below.

The first RICC-advancing step includes pushing the catheter-advancement push tab 170 with the single finger of the hand while holding the distal portion of the syringe 162 between the thumb and the other finger or fingers of the same hand to advance the distal portion of the first section 132 of the catheter tube 114 into the blood-vessel lumen over the needle shaft. Again, the catheter-advancement push tab 170 is part of the catheter-advancement hub 158 coupled to the proximal portion of the distal catheter piece 104 in the ready-to-deploy state of the introducer assembly 154.

The introducer housing-splitting step includes unlocking the lock 180 in the distal portion of the introducer housing 160 then splitting the introducer housing 160 along its length. Unlocking the lock 180 includes separating the hook 182 of the slidable piece 176 of the introducer housing 160 and the latch 184 of the stationary piece 178 of the introducer housing 160 by distally sliding the slidable piece 176 relative to the stationary piece 178. While the lock 180 can be manually unlocked by sliding the slidable piece 176 relative to the stationary piece 178, the introducer assembly 154 is configured such that pushing the catheter-advancement push tab 170 of the catheter-advancement hub 158 against the introducer-housing tab 196 slides the slidable piece 176 relative to the stationary piece 178. Unlocking the lock 180 in accordance with the latter while holding the introducer assembly 154 about the distal portion of the syringe 162 minimizes problems associated with overhandling the introducer assembly 154 such as fumbling and dropping the introducer assembly 154 or contaminating any exposed portion of the catheter tube 114 of the distal catheter piece 104 in the introducer assembly 154.

As to splitting the introducer housing 160, the stationary piece 178 of the introducer housing 160 includes the channel 186 including the latch 184 in the proximal portion of the channel 186 and the ramp 188 in the distal portion of the channel 186 as set forth above. Distally sliding the slidable piece 176 relative to the stationary piece 178 causes the distal face of the hook 182 to engage the proximal face of the ramp 188 and split the introducer housing 160 along its length as the hook 182 is lifted out of the channel 186. While the introducer housing 160 can be manually split by sliding the slidable piece 176 relative to the stationary piece 178, the introducer assembly 154 is configured such that pushing the catheter-advancement push tab 170 of the catheter-advancement hub 158 advances the side arm 168 of the catheter-advancement hub 158 along the path provided by the longitudinal cutout 198 of the introducer housing 160. Because the longitudinal cutout 198 narrows from the proximal portion to the distal portion of the introducer housing 160, the side arm 168 of the catheter-advancement hub 158 continues to lift and separate the slidable piece 176 from the stationary piece 178 until the side arm 168 exits the longitudinal cutout 198.

The introducer-removing step includes removing the distal catheter piece 104 from the introducer housing 160, withdrawing the introducer 156 from the distal catheter piece 104, and leaving the distal portion of the first section 132 of the catheter tube 114 in place in the blood-vessel lumen. Withdrawing the introducer 156 from the distal catheter piece 104 includes withdrawing both the needle shaft and the access guidewire 222 from the distal catheter piece 104.

The method further includes a catheter hub-clipping step. The catheter hub-clipping step includes clipping together the proximal catheter-hub piece 106 of the proximal catheter piece 102 and the distal catheter-hub piece 112 of the distal catheter piece 104. The catheter hub-clipping step respectively connects the one-or-more extension-leg lumens of the one-or-more extension legs 110 coupled to the proximal catheter-hub piece 106 to the one-or-more catheter-tube lumens of the catheter tube 114, thereby forming the RICC 100 and the lumens thereof across the two-piece catheter hub 108.

The method can further include a maneuver guidewire-advancing step. The maneuver guidewire-advancing step includes advancing a maneuver guidewire into the blood-vessel lumen to a target location (e.g., the SVC) in a vasculature of the patient by way of the primary lumen 142 of the RICC 100 having the primary-lumen aperture 144 in the distal end of the RICC 100.

The method can further include a second RICC-advancing step and a maneuver guidewire-removing step. The second RICC-advancing step includes advancing a remainder of the distal portion of the first section 132 of the catheter tube 114 farther into the blood-vessel lumen up to a proximal portion of the second section 134 of the catheter tube 114 using the maneuver guidewire as a guide. The maneuver guidewire provides the second section 134 of the catheter tube 114 columnar strength for the second RICC-advancing step. The second RICC-advancing step is stopped with respect to the advancing when the distal end of the distal catheter piece 104 arrives at the target location. (e.g., the SVC) The maneuver guidewire-removing step includes withdrawing the maneuver guidewire and leaving the catheter tube 114 in place in the patient.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A rapidly insertable central catheter ("RICC") system, comprising:
 a distal catheter piece of a RICC including:
  a distal catheter-hub piece of a two-piece catheter hub; and
  a catheter tube including one or more catheter-tube lumens, the catheter tube coupled to the distal catheter-hub piece by a proximal portion of the catheter tube; and
 an introducer configured to combine with the distal catheter piece in an introducer assembly having a ready-to-deploy state configured to be actuated with a single finger of a hand while the introducer is held between a thumb and a finger or fingers of the hand, the introducer including:
  a catheter-advancement hub including a manifold and a side arm, the catheter-advancement hub coupled to a proximal portion of the distal catheter-hub piece in the ready-to-deploy state of the introducer assembly;
  an introducer needle having a needle shaft extending through the manifold and a distal end of the distal catheter piece in the ready-to-deploy state of the introducer assembly;
  a syringe including a barrel having a distal portion terminating in a syringe tip, the syringe fluidly coupled to the introducer needle proximal of the introducer needle; wherein the barrel is aligned with a longitudinal axis of the introducer; and
 an introducer housing over the syringe tip, the manifold, and the proximal portion of the distal catheter piece in the ready-to-deploy state of the introducer assembly, the introducer housing configured to:
  provide column strength to the catheter tube during a venipuncture on a patient with the introducer needle; and
  longitudinally split allowing the distal catheter piece to be removed from the introducer housing after the venipuncture.

2. The RICC system of claim 1, wherein the introducer housing includes a lock in a distal portion of the introducer housing including a hook of a slidable piece of the introducer housing and a latch of a stationary piece of the introducer housing, the hook and the latch configured to lock the slidable piece and the stationary piece together in the ready-to-deploy state of the introducer assembly.

3. The RICC system of claim 2, wherein the stationary piece of the introducer housing includes a channel including the latch in a proximal portion of the channel and a ramp in a distal portion of the channel, a combination of the hook and the ramp configured to push the slidable piece of the introducer housing away from the stationary piece when a distal face of the hook engages a proximal face of the ramp while distally advancing the slidable piece relative to the stationary piece.

4. The RICC system of claim 2, wherein the introducer housing includes a sliding hinge in a proximal portion of the introducer housing including a captive tab of the slidable piece of the introducer housing and a track of the stationary piece of the introducer housing, the captive tab captively but slidably disposed in the track allowing the slidable piece to be distally advanced relative to the stationary piece without separating the slidable piece from the stationary piece in the proximal portion of the introducer housing.

5. The RICC system of claim 4, wherein a proximal portion of the captive tab inboard of an exterior surface of the introducer housing is radiused to facilitate splitting the slidable piece of the introducer housing from the stationary piece of the introducer housing in the distal portion of the introducer housing.

6. The RICC system of claim 4, wherein the proximal portion of the introducer housing includes a longitudinal cutout configured to provide a path for the side arm of the catheter-advancement hub while distally advancing the catheter-advancement hub within the introducer housing.

7. The RICC system of claim 1, wherein the manifold includes one or more manifold lumens equal in number to the one or more catheter-tube lumens, the one or more manifold lumens fluidly connected to the one or more catheter-tube lumens in the ready-to-deploy state of the introducer assembly.

8. The RICC system of claim 7, wherein the side arm of the catheter-advancement hub includes a side-arm lumen fluidly coupled to the one or more manifold lumens for simultaneously priming each lumen of the one or more catheter-tube lumens before inserting the catheter tube into a blood-vessel lumen of the patient.

9. The RICC system of claim 1, the catheter-advancement hub further including a catheter-advancement push tab extending from the side arm configured for distally advancing the catheter-advancement hub with the single finger of the hand while holding the syringe around the distal portion of the barrel between the thumb and the finger or fingers of the hand.

10. The RICC system of claim 1, further comprising a proximal catheter piece of the RICC including:

a proximal catheter-hub piece of the two-piece catheter hub; and one or more extension legs respectively including one or more extension-leg lumens, each extension leg of the one or more extension legs coupled to the proximal catheter-hub piece by a distal portion of each extension leg, wherein the RICC has a connected state in which the proximal catheter-hub piece is connected to the distal catheter-hub piece such that the one or more extension-leg lumens are respectively fluidly coupled to the one or more catheter-tube lumens across the two-piece catheter hub.

11. The RICC system of claim 10, wherein the RICC includes a set of three lumens in the connected state of the RICC, the set of three lumens including a primary lumen, a secondary lumen, and a tertiary lumen.

12. The RICC system of claim 11, wherein the primary lumen has a primary-lumen aperture in a distal end of the two-piece catheter hub, the secondary lumen has a secondary-lumen aperture in a side of the catheter tube proximal of the primary-lumen aperture, and the tertiary lumen has a tertiary-lumen aperture in the side of the catheter tube proximal of the secondary-lumen aperture.

13. The RICC system of claim 1, the catheter tube further including:

a first section formed of a first material having a first durometer; and a second section formed of a second material having a second durometer less than the first durometer, the catheter tube thereby configured with both column strength for inserting the catheter tube into the patient and compliance for advancing the catheter tube through a vasculature of the patient.

14. The RICC system of claim 1, the introducer further including a syringe housing around the barrel of the syringe having a distal portion and a proximal portion, the proximal portion of the syringe housing either integral with or coupled to a proximal portion of a plunger disposed in the barrel such that proximally sliding the syringe housing relative to the barrel withdraws the plunger from the barrel.

15. The RICC system of claim 14, the syringe further including a plunger-withdrawal push tab proximally extending over the barrel from the distal portion of the barrel to which the plunger-withdrawal push tab is coupled, the plunger-withdrawal push tab configured for pushing against with the single finger of the hand while holding the syringe around the distal portion of the barrel between the thumb and the finger or fingers of the hand to proximally slide the syringe housing relative to the barrel and withdraw the plunger from the barrel.

16. The RICC system of claim 14, the introducer further including an access guidewire disposed in an access-guidewire lumen formed of at least a plunger lumen of the plunger and a needle lumen of the introducer needle, the access guidewire having a length sufficient for extension of the access guidewire through the distal end of the distal catheter piece.

17. The RICC system of claim 16, the introducer further including a slider distally extending over the barrel from the syringe housing configured for actuating the access guidewire with the single finger of the hand while holding the syringe around the distal portion of the barrel between the thumb and the finger or fingers of the hand, the slider including an extension extending through a longitudinal slot in each of the barrel and the plunger into the access-guidewire lumen where the extension is coupled to the access guidewire.

18. An introducer for a rapidly insertable central catheter ("RICC"), comprising:

a catheter-advancement hub including a manifold and a side arm, the catheter-advancement hub configured to couple to a distal catheter piece of the RICC in an introducer assembly;

an introducer needle having a needle shaft configured to extend through the manifold and a distal end of the distal catheter piece in a ready-to-deploy state of the introducer assembly;

a syringe fluidly coupled to the introducer needle proximal of the introducer needle, the syringe including a barrel having a distal portion terminating in a syringe tip, wherein the barrel is aligned with a longitudinal axis of the introducer, the syringe configured to be held around the distal portion of the barrel between a thumb and a finger or fingers of a hand while reserving a single finger for actuating the introducer;

an access guidewire disposed in an introducer-needle portion of an access-guidewire lumen formed of a needle lumen of the introducer needle; and an introducer housing over the syringe tip, the manifold, and a proximal portion of the distal catheter piece in the ready-to-deploy state of the introducer assembly, the introducer housing configured to:

provide column strength to a catheter tube of the distal catheter piece during a venipuncture on a patient with the introducer needle; and longitudinally split allowing the distal catheter piece to be removed from the introducer housing after the venipuncture.

19. The introducer of claim 18, wherein the introducer housing includes a lock in a distal portion of the introducer housing including a hook of a slidable piece of the introducer housing and a latch of a stationary piece of the introducer housing, the hook and the latch configured to lock the slidable piece and the stationary piece together.

20. The introducer of claim 19, wherein the stationary piece of the introducer housing includes a channel including the latch in a proximal portion of the channel and a ramp in a distal portion of the channel, a combination of the hook and the ramp configured to push the slidable piece of the introducer housing away from the stationary piece when a distal face of the hook engages a proximal face of the ramp while distally advancing the slidable piece relative to the stationary piece.

21. The introducer of claim 19, wherein the introducer housing includes a sliding hinge in a proximal portion of the introducer housing including a captive tab of the slidable piece of the introducer housing and a track of the stationary piece of the introducer housing, the captive tab captively but slidably disposed in the track allowing the slidable piece to be distally advanced relative to the stationary piece without separating the slidable piece from the stationary piece in the proximal portion of the introducer housing.

22. The introducer of claim 21, wherein a proximal portion of the captive tab inboard of an exterior surface of the introducer housing is radiused to facilitate splitting the slidable piece of the introducer housing from the stationary piece of the introducer housing in the distal portion of the introducer housing.

23. The introducer of claim 21, wherein the proximal portion of the introducer housing includes a longitudinal cutout configured to provide a path for the side arm of the catheter-advancement hub while distally advancing the catheter-advancement hub within the introducer housing.

24. The introducer of claim 18, wherein the side arm of the catheter-advancement hub includes a side-arm lumen fluidly coupled to one or more manifold lumens for simultaneously priming each lumen of one or more lumens of the distal catheter piece of the RICC in the ready-to-deploy state of the introducer assembly.

25. The introducer of claim 18, the catheter-advancement hub further including a catheter-advancement push tab extending from the side arm configured for distally advancing the catheter-advancement hub with the single finger of the hand while holding the syringe around the distal portion of the barrel between the thumb and the finger or fingers of the hand.

26. The introducer of claim 18, the introducer further including a syringe housing around the barrel of the syringe having a distal portion and a proximal portion, the proximal portion of the syringe housing either integral with or coupled to a proximal portion of a plunger disposed in the barrel such that proximally sliding the syringe housing relative to the barrel withdraws the plunger from the barrel.

27. The introducer of claim 26, the syringe further including a plunger-withdrawal push tab proximally extending over the barrel from the distal portion of the barrel to which the plunger-withdrawal push tab is coupled, the plunger-withdrawal push tab configured for pushing against with the single finger of the hand while holding the syringe around the distal portion of the barrel between the thumb and the finger or fingers of the hand to proximally slide the syringe housing relative to the barrel and withdraw the plunger from the barrel.

28. The introducer of claim 26, wherein the access guidewire is further disposed in a syringe portion of the access-guidewire lumen formed of at least a plunger lumen of the plunger, the access guidewire having a length sufficient for extension of the access guidewire through a distal end of the distal catheter piece in the ready-to-deploy state of the introducer assembly.

29. The introducer of claim 28, the introducer further including a slider distally extending over the barrel from the syringe housing configured for actuating the access guidewire with the single finger of the hand while holding the syringe around the distal portion of the barrel between the thumb and the finger or fingers of the hand, the slider including an extension extending through a longitudinal slot in each of the barrel and the plunger into the access-guidewire lumen where the extension is coupled to the access guidewire.

30. A rapidly insertable central catheter ("RICC") system, comprising:

a RICC including:

a distal catheter piece including a distal catheter-hub piece of a two-piece catheter hub and a catheter tube coupled to the distal catheter-hub piece; and a proximal catheter piece including a proximal catheter-hub piece of the two-piece catheter hub; and an introducer configured to combine with the distal catheter piece in an introducer assembly for a venipuncture on a patient, the introducer including:

a catheter-advancement hub including a manifold and a side arm, the catheter-advancement hub coupled to a proximal portion of the distal catheter-hub piece in a ready-to-deploy state of the introducer assembly;

an introducer needle having a needle shaft extending through the manifold and a distal end of the distal catheter piece in the ready-to-deploy state of the introducer assembly;

a syringe proximally and fluidly coupled to the introducer needle by way of a syringe tip; the syringe including a barrel, wherein the barrel is aligned with a longitudinal axis of the introducer; and an introducer housing over the syringe tip, the manifold, and a proximal portion of the distal catheter piece in the ready-to-deploy state of the introducer assembly, the introducer housing configured to longitudinally split allowing the distal catheter piece to be removed from the introducer housing after the venipuncture for clipping the proximal catheter piece together with the distal catheter piece by way of the two-piece catheter hub.

31. The RICC system of claim 30, wherein the catheter tube of the distal catheter piece includes a plurality of catheter-tube lumens, the manifold includes a plurality of manifold lumens equal in number to the plurality of catheter-tube lumens, and the plurality of manifold lumens is fluidly connected to the plurality of catheter-tube lumens in the ready-to-deploy state of the introducer assembly.

32. The RICC system of claim 31, wherein the side arm of the catheter-advancement hub includes a side-arm lumen fluidly coupled to the plurality of manifold lumens for simultaneously priming each lumen of the plurality of catheter-tube lumens before inserting the catheter tube into a blood-vessel lumen of the patient.

33. The RICC system of claim 30, the introducer further including an access guidewire disposed in an introducer-needle portion of an access-guidewire lumen formed of a needle lumen of the introducer needle.

34. The RICC system of claim 33, wherein the access guidewire is further disposed in a syringe portion of the access-guidewire lumen formed of at least a plunger lumen of a plunger of the syringe, the access guidewire having a length sufficient for extension of the access guidewire through a distal end of the distal catheter piece in the ready-to-deploy state of the introducer assembly.

\*    \*    \*    \*    \*